United States Patent
Fulton, III

(10) Patent No.: US 12,357,314 B2
(45) Date of Patent: Jul. 15, 2025

(54) LOW RADIAL FORCE VASCULAR DEVICE AND METHOD OF OCCLUSION

(71) Applicant: Vascular Development Corp, LLC, Grand Junction, CO (US)

(72) Inventor: Richard E. Fulton, III, Grand Junction, CO (US)

(73) Assignee: Vascular Development Corp, LLC, Grand Junction, CO (US)

( * ) Notice: Subject to any disclaimer, the term of this patent is extended or adjusted under 35 U.S.C. 154(b) by 0 days.

(21) Appl. No.: 17/586,562

(22) Filed: Jan. 27, 2022

(65) Prior Publication Data

US 2022/0361885 A1   Nov. 17, 2022

Related U.S. Application Data

(63) Continuation of application No. 16/226,832, filed on Dec. 20, 2018, now Pat. No. 11,266,414, which is a
(Continued)

(51) Int. Cl.
 *A61B 17/12* (2006.01)
 *A61B 17/221* (2006.01)
 (Continued)

(52) U.S. Cl.
 CPC .... *A61B 17/1204* (2013.01); *A61B 17/12109* (2013.01); *A61B 17/12131* (2013.01);
 (Continued)

(58) Field of Classification Search
 CPC .......... A61B 17/1204; A61B 17/12109; A61B 17/12131; A61B 17/12168;
 (Continued)

(56) References Cited

U.S. PATENT DOCUMENTS

| | | |
|---|---|---|
| 2,230,226 A | 2/1941 | Auzin |
| 2,259,488 A | 10/1941 | Raiche |

(Continued)

FOREIGN PATENT DOCUMENTS

| | | |
|---|---|---|
| EP | 0983749 A2 | 3/2000 |
| EP | 1030603 A1 | 8/2000 |

(Continued)

OTHER PUBLICATIONS

EP 14894131.3 Extended European Search Report and Search Opinion dated Jan. 17, 2018.
(Continued)

*Primary Examiner* — Sarah W Aleman
(74) *Attorney, Agent, or Firm* — Wilson Sonsini Goodrich & Rosati

(57) ABSTRACT

An occlusion apparatus comprises inner and outer sheaths and an expandable flexible tubular sleeve. The occlusion apparatus is advanced to a target site in the blood vessel. A dilator having a soft, compressible tip may be advanced through a lumen of the inner sheath to facilitate the advancement of the occlusion apparatus. The sheaths are translated relative to one another to expand the flexible tubular sleeve to a funnel shape with a distal flush portion contacting the blood vessel inner wall and a proximal tapered portion. The proximal portion is fluid permeable so that blood can pass through to apply pressure on the vessel wall through the distal portion. A capture or traction device can be advanced out of the inner sheath lumen and retracted back therein to capture thrombus. The distal portion of the device may comprise an expandable mesh braid with a memory characteristic to limit expansion.

30 Claims, 9 Drawing Sheets

Related U.S. Application Data continuation of application No. 14/554,348, filed on Nov. 26, 2014, now abandoned.

(60) Provisional application No. 62/007,553, filed on Jun. 4, 2014.

(51) Int. Cl.
 *A61B 17/22* (2006.01)
 *A61F 2/01* (2006.01)

(52) U.S. Cl.
 CPC ...... *A61B 17/12168* (2013.01); *A61B 17/221* (2013.01); *A61B 2017/1205* (2013.01); *A61B 17/12177* (2013.01); *A61B 2017/22067* (2013.01); *A61F 2/013* (2013.01)

(58) Field of Classification Search
 CPC . A61B 17/12172; A61B 17/22; A61B 17/221; A61F 2/01; A61F 2/0108; A61F 2/013
 See application file for complete search history.

(56) References Cited

U.S. PATENT DOCUMENTS

| | | |
|---|---|---|
| 3,050,066 A | 8/1962 | Koehn |
| 3,540,431 A | 11/1970 | Kazi |
| 3,799,172 A | 3/1974 | Szpur |
| 3,831,587 A | 8/1974 | Boyd |
| 3,834,394 A | 9/1974 | Hunter et al. |
| 3,952,747 A | 4/1976 | Kimmell, Jr. |
| 3,978,863 A | 9/1976 | Fettel et al. |
| 3,996,938 A | 12/1976 | Clark, III |
| 4,030,503 A | 6/1977 | Clark, III |
| 4,372,293 A | 2/1983 | Vijil-Rosales |
| 4,401,124 A | 8/1983 | Guess et al. |
| 4,425,908 A | 1/1984 | Simon |
| 4,445,892 A | 5/1984 | Hussein et al. |
| 4,494,531 A | 1/1985 | Gianturco |
| 4,573,966 A | 3/1986 | Weikl et al. |
| 4,581,017 A | 4/1986 | Sahota et al. |
| 4,582,061 A | 4/1986 | Fry |
| 4,606,347 A | 8/1986 | Fogarty et al. |
| 4,608,965 A | 9/1986 | Anspach, Jr. et al. |
| 4,611,594 A | 9/1986 | Grayhack et al. |
| 4,621,636 A | 11/1986 | Fogarty |
| 4,646,736 A | 3/1987 | Auth |
| 4,650,466 A | 3/1987 | Luther |
| 4,696,304 A | 9/1987 | Chin |
| 4,727,873 A | 3/1988 | Mobin-Uddin |
| 4,762,130 A | 8/1988 | Fogarty et al. |
| 4,793,348 A | 12/1988 | Palmaz |
| 4,794,925 A | 1/1989 | Mori |
| 4,794,928 A | 1/1989 | Kletschka |
| 4,799,495 A | 1/1989 | Hawkins et al. |
| 4,820,270 A | 4/1989 | Hardcastle et al. |
| 4,832,055 A | 5/1989 | Palestrant |
| 4,858,810 A | 8/1989 | Intlekofer et al. |
| 4,869,259 A | 9/1989 | Elkins |
| 4,895,560 A | 1/1990 | Papantonakos |
| 4,921,478 A | 5/1990 | Solano et al. |
| 4,921,484 A | 5/1990 | Hillstead |
| 4,926,858 A | 5/1990 | Gifford, III et al. |
| 4,946,440 A | 8/1990 | Hall |
| 4,977,897 A | 12/1990 | Hurwitz |
| 5,011,488 A | 4/1991 | Ginsburg |
| 5,048,530 A | 9/1991 | Hurwitz |
| 5,059,166 A | 10/1991 | Fischell et al. |
| 5,078,685 A | 1/1992 | Colliver |
| 5,081,997 A | 1/1992 | Bosley, Jr. et al. |
| 5,092,839 A | 3/1992 | Kipperman |
| 5,100,425 A | 3/1992 | Fischell et al. |
| 5,102,415 A | 4/1992 | Guenther et al. |
| 5,108,420 A | 4/1992 | Marks |
| 5,112,347 A | 5/1992 | Taheri |
| 5,116,352 A | 5/1992 | Schnepp-Pesch et al. |
| 5,135,484 A | 8/1992 | Wright |
| 5,171,305 A | 12/1992 | Schickling et al. |
| 5,176,659 A | 1/1993 | Mancini |
| 5,183,463 A | 2/1993 | Debbas |
| 5,183,464 A | 2/1993 | Dubrul et al. |
| 5,192,290 A | 3/1993 | Hilal |
| 5,209,727 A | 5/1993 | Radisch, Jr. et al. |
| 5,213,569 A | 5/1993 | Davis |
| 5,221,269 A | 6/1993 | Miller et al. |
| 5,226,909 A | 7/1993 | Evans et al. |
| 5,250,060 A | 10/1993 | Carbo et al. |
| 5,275,611 A | 1/1994 | Behl |
| 5,312,360 A | 5/1994 | Behl |
| 5,328,471 A | 7/1994 | Slepian |
| 5,329,942 A | 7/1994 | Gunther et al. |
| 5,330,482 A | 7/1994 | Gibbs et al. |
| 5,330,484 A | 7/1994 | Guenther et al. |
| 5,334,211 A | 8/1994 | Shiber |
| 5,336,205 A | 8/1994 | Zenzen et al. |
| 5,342,306 A | 8/1994 | Don Michael |
| 5,370,660 A | 12/1994 | Weinstein et al. |
| 5,380,273 A | 1/1995 | Dubrul et al. |
| 5,380,284 A | 1/1995 | Don Michael |
| 5,382,259 A | 1/1995 | Phelps et al. |
| 5,383,466 A | 1/1995 | Partika |
| 5,383,897 A | 1/1995 | Wholey |
| 5,397,307 A | 3/1995 | Goodin |
| 5,410,093 A | 4/1995 | Dorai |
| 5,419,774 A | 5/1995 | Willard et al. |
| 5,423,799 A | 6/1995 | Shiu |
| 5,431,676 A | 7/1995 | Dubrul et al. |
| 5,437,631 A | 8/1995 | Janzen |
| 5,441,485 A | 8/1995 | Peters |
| 5,443,454 A | 8/1995 | Tanabe et al. |
| 5,454,790 A | 10/1995 | Dubrul |
| 5,456,667 A | 10/1995 | Ham et al. |
| 5,462,529 A | 10/1995 | Simpson et al. |
| 5,483,976 A | 1/1996 | McLaughlin et al. |
| 5,490,521 A | 2/1996 | Davis et al. |
| 5,496,275 A | 3/1996 | Sirhan et al. |
| 5,497,782 A | 3/1996 | Fugoso |
| 5,498,236 A | 3/1996 | Dubrul et al. |
| 5,501,408 A | 3/1996 | Kang et al. |
| 5,518,498 A | 5/1996 | Lindenberg et al. |
| 5,527,282 A | 6/1996 | Segal |
| 5,540,658 A | 7/1996 | Evans et al. |
| 5,549,626 A | 8/1996 | Miller et al. |
| 5,556,408 A | 9/1996 | Farhat |
| 5,569,275 A | 10/1996 | Kotula et al. |
| 5,569,277 A | 10/1996 | Evans et al. |
| 5,571,135 A | 11/1996 | Fraser et al. |
| 5,591,204 A | 1/1997 | Janzen et al. |
| 5,606,979 A | 3/1997 | Hodgson |
| 5,611,345 A | 3/1997 | Hibbeln |
| 5,626,614 A | 5/1997 | Hart |
| 5,632,754 A | 5/1997 | Farley et al. |
| 5,643,282 A | 7/1997 | Kieturakis |
| 5,653,684 A | 8/1997 | Laptewicz et al. |
| 5,653,689 A | 8/1997 | Buelna et al. |
| 5,662,671 A | 9/1997 | Barbut et al. |
| 5,662,703 A | 9/1997 | Yurek et al. |
| 5,681,335 A | 10/1997 | Serra et al. |
| 5,683,411 A | 11/1997 | Kavteladze et al. |
| 5,683,451 A | 11/1997 | Lenker et al. |
| 5,695,501 A | 12/1997 | Carol et al. |
| 5,695,507 A | 12/1997 | Auth et al. |
| 5,709,697 A | 1/1998 | Ratcliff et al. |
| 5,709,704 A | 1/1998 | Nott et al. |
| 5,713,848 A | 2/1998 | Dubrul et al. |
| 5,730,733 A | 3/1998 | Mortier et al. |
| 5,733,294 A | 3/1998 | Forber et al. |
| 5,738,652 A | 4/1998 | Boyd et al. |
| 5,749,883 A | 5/1998 | Halpern |
| 5,766,135 A | 6/1998 | Terwilliger |
| 5,766,191 A | 6/1998 | Trerotola |
| 5,766,203 A | 6/1998 | Imran et al. |
| 5,769,795 A | 6/1998 | Terwilliger |
| 5,769,871 A | 6/1998 | Mers et al. |
| 5,779,672 A | 7/1998 | Dormandy, Jr. |

(56) References Cited

U.S. PATENT DOCUMENTS

| | | |
|---|---|---|
| 5,792,157 A | 8/1998 | Mische et al. |
| 5,795,308 A | 8/1998 | Russin |
| 5,795,322 A | 8/1998 | Boudewijn |
| 5,797,960 A | 8/1998 | Stevens et al. |
| 5,814,064 A | 9/1998 | Daniel et al. |
| 5,827,324 A | 10/1998 | Cassell et al. |
| 5,833,650 A | 11/1998 | Imran |
| 5,843,022 A | 12/1998 | Willard et al. |
| 5,846,251 A | 12/1998 | Hart |
| 5,851,210 A | 12/1998 | Torossian |
| 5,853,422 A | 12/1998 | Huebsch et al. |
| 5,868,708 A | 2/1999 | Hart et al. |
| 5,897,567 A | 4/1999 | Ressemann et al. |
| 5,904,698 A | 5/1999 | Thomas et al. |
| 5,908,435 A | 6/1999 | Samuels |
| 5,910,150 A | 6/1999 | Saadat |
| 5,916,235 A | 6/1999 | Guglielmi |
| 5,928,186 A | 7/1999 | Homsma et al. |
| 5,928,260 A | 7/1999 | Chin et al. |
| 5,935,139 A | 8/1999 | Bates |
| 5,947,985 A | 9/1999 | Imran |
| 5,947,995 A | 9/1999 | Samuels |
| 5,954,737 A | 9/1999 | Lee |
| 5,972,019 A | 10/1999 | Engelson et al. |
| 5,997,503 A | 12/1999 | Willis et al. |
| 6,001,118 A | 12/1999 | Daniel et al. |
| 6,027,520 A | 2/2000 | Tsugita et al. |
| 6,053,876 A | 4/2000 | Fisher |
| 6,053,900 A | 4/2000 | Brown et al. |
| 6,066,158 A * | 5/2000 | Engelson ............ A61B 17/221 606/159 |
| 6,086,605 A | 7/2000 | Barbut et al. |
| 6,096,053 A | 8/2000 | Bates |
| 6,156,005 A | 12/2000 | Theron |
| 6,161,034 A | 12/2000 | Burbank et al. |
| 6,179,860 B1 | 1/2001 | Fulton, III et al. |
| 6,206,868 B1 | 3/2001 | Parodi |
| 6,217,600 B1 | 4/2001 | DiMatteo |
| 6,221,006 B1 | 4/2001 | Dubrul et al. |
| 6,221,086 B1 | 4/2001 | Forber |
| 6,231,544 B1 | 5/2001 | Tsugita et al. |
| 6,238,412 B1 | 5/2001 | Dubrul et al. |
| 6,258,115 B1 | 7/2001 | Dubrul |
| 6,277,083 B1 | 8/2001 | Eggers et al. |
| 6,280,414 B1 | 8/2001 | Shah et al. |
| 6,287,271 B1 | 9/2001 | Dubrul et al. |
| 6,356,782 B1 | 3/2002 | Sirimanne et al. |
| 6,361,545 B1 | 3/2002 | Macoviak et al. |
| 6,375,634 B1 | 4/2002 | Carroll |
| 6,413,235 B1 | 7/2002 | Parodi |
| 6,423,032 B2 | 7/2002 | Parodi et al. |
| 6,443,971 B1 | 9/2002 | Boylan et al. |
| 6,450,989 B2 | 9/2002 | Dubrul et al. |
| 6,485,501 B1 | 11/2002 | Green |
| 6,524,301 B1 | 2/2003 | Wilson et al. |
| 6,530,923 B1 | 3/2003 | Dubrul et al. |
| 6,540,768 B1 | 4/2003 | Diaz et al. |
| 6,544,278 B1 | 4/2003 | Vrba et al. |
| 6,602,204 B2 | 8/2003 | Dubrul et al. |
| 6,605,102 B1 * | 8/2003 | Mazzocchi ............ A61B 17/221 606/200 |
| 6,626,886 B1 | 9/2003 | Barbut |
| 6,635,068 B1 | 10/2003 | Dubrul et al. |
| 6,656,202 B2 | 12/2003 | Papp et al. |
| 6,660,014 B2 | 12/2003 | Demarais et al. |
| 6,695,858 B1 | 2/2004 | Dubrul et al. |
| 6,699,260 B2 | 3/2004 | Dubrul et al. |
| 6,740,094 B2 | 5/2004 | Maitland et al. |
| 6,852,097 B1 | 2/2005 | Fulton, III |
| 6,929,652 B1 | 8/2005 | Andrews et al. |
| 6,945,977 B2 | 9/2005 | Demarais et al. |
| 6,994,677 B1 | 2/2006 | Buehlmann et al. |
| 7,201,770 B2 | 4/2007 | Johnson et al. |
| 7,220,269 B1 * | 5/2007 | Ansel ............ A61B 17/22032 604/35 |
| 7,232,432 B2 | 6/2007 | Fulton et al. |
| 7,232,453 B2 | 6/2007 | Shimon |
| 7,241,257 B1 | 7/2007 | Ainsworth et al. |
| 7,374,561 B2 | 5/2008 | Barbut |
| 7,422,579 B2 | 9/2008 | Wahr et al. |
| 7,534,251 B2 | 5/2009 | Wasdyke |
| 7,569,071 B2 | 8/2009 | Haverkost et al. |
| 7,645,296 B2 | 1/2010 | Theron et al. |
| 7,670,368 B2 | 3/2010 | Hill et al. |
| 7,686,825 B2 | 3/2010 | Hauser et al. |
| 7,780,722 B2 | 8/2010 | Thielen et al. |
| 7,803,171 B1 | 9/2010 | Uflacker |
| 7,867,274 B2 | 1/2011 | Hill et al. |
| 7,951,189 B2 | 5/2011 | Haverkost et al. |
| 7,959,603 B2 | 6/2011 | Wahr et al. |
| 8,366,737 B2 | 2/2013 | Hancock et al. |
| 8,657,849 B2 | 2/2014 | Parker |
| 8,663,273 B2 | 3/2014 | Khairkhahan et al. |
| 8,715,317 B1 * | 5/2014 | Janardhan ........ A61B 17/12109 606/200 |
| 8,740,961 B2 | 6/2014 | Fulton, III |
| 8,771,289 B2 | 7/2014 | Mohiuddin et al. |
| 8,777,976 B2 | 7/2014 | Brady et al. |
| 8,784,441 B2 | 7/2014 | Rosenbluth et al. |
| 8,795,305 B2 * | 8/2014 | Martin ............... A61B 17/3207 606/159 |
| 8,900,257 B2 | 12/2014 | Straub et al. |
| 9,114,031 B2 | 8/2015 | Fulton, III |
| 9,126,016 B2 | 9/2015 | Fulton et al. |
| 9,186,487 B2 | 11/2015 | Dubrul et al. |
| 9,211,396 B2 | 12/2015 | Aboytes |
| 9,498,604 B2 | 11/2016 | Dubrul et al. |
| 9,561,094 B2 | 2/2017 | Fulton |
| 10,335,577 B2 | 7/2019 | Richard |
| 11,266,414 B2 | 3/2022 | Fulton, III |
| 11,623,070 B2 | 4/2023 | Richard |
| 2002/0007130 A1 | 1/2002 | Burbank et al. |
| 2002/0016555 A1 | 2/2002 | Ritchart et al. |
| 2002/0019640 A1 | 2/2002 | McGuckin et al. |
| 2002/0022859 A1 | 2/2002 | Hogendijk |
| 2002/0026201 A1 | 2/2002 | Foerster et al. |
| 2002/0045916 A1 | 4/2002 | Gray et al. |
| 2002/0095169 A1 | 7/2002 | Maitland et al. |
| 2002/0161394 A1 | 10/2002 | Macoviak et al. |
| 2002/0165574 A1 | 11/2002 | Ressemann et al. |
| 2002/0165598 A1 | 11/2002 | Wahr et al. |
| 2003/0023204 A1 | 1/2003 | Vo et al. |
| 2003/0083608 A1 | 5/2003 | Evans et al. |
| 2003/0109896 A1 | 6/2003 | Dubrul et al. |
| 2003/0114879 A1 | 6/2003 | Euteneuer et al. |
| 2003/0163158 A1 | 8/2003 | White |
| 2003/0176884 A1 | 9/2003 | Berrada et al. |
| 2004/0015150 A1 | 1/2004 | Zadno-Azizi |
| 2004/0044391 A1 | 3/2004 | Porter |
| 2004/0153117 A1 | 8/2004 | Clubb et al. |
| 2004/0181237 A1 | 9/2004 | Forde et al. |
| 2004/0199202 A1 | 10/2004 | Dubrul et al. |
| 2004/0236369 A1 | 11/2004 | Dubrul |
| 2004/0260332 A1 | 12/2004 | Dubrul et al. |
| 2004/0260333 A1 | 12/2004 | Dubrul et al. |
| 2005/0018757 A1 | 1/2005 | Zaccheo et al. |
| 2005/0038447 A1 | 2/2005 | Huffmaster |
| 2005/0059993 A1 | 3/2005 | Ramzipoor et al. |
| 2005/0165366 A1 * | 7/2005 | Brustad ............ A61M 25/0043 604/264 |
| 2005/0187570 A1 * | 8/2005 | Nguyen ........... A61B 17/32056 606/159 |
| 2005/0277976 A1 | 12/2005 | Galdonik et al. |
| 2006/0047286 A1 | 3/2006 | West |
| 2006/0058836 A1 | 3/2006 | Bose et al. |
| 2006/0085065 A1 | 4/2006 | Krause et al. |
| 2006/0200074 A1 | 9/2006 | Zadno-Azizi |
| 2006/0253145 A1 | 11/2006 | Lucas |
| 2007/0123932 A1 * | 5/2007 | Gray ....................... A61F 2/013 606/200 |
| 2007/0126161 A1 | 6/2007 | Gray et al. |
| 2007/0142858 A1 | 6/2007 | Bates |
| 2007/0233175 A1 | 10/2007 | Zaver et al. |
| 2008/0058794 A1 | 3/2008 | MacAdam et al. |

(56) References Cited

U.S. PATENT DOCUMENTS

| | | |
|---|---|---|
| 2008/0058800 A1 | 3/2008 | Collins et al. |
| 2008/0119888 A1 | 5/2008 | Huffmaster |
| 2009/0264976 A1* | 10/2009 | Nagasrinivasa ...... A61M 29/02 623/1.11 |
| 2010/0030256 A1* | 2/2010 | Dubrul ............. A61B 17/12113 606/200 |
| 2010/0114113 A1 | 5/2010 | Dubrul et al. |
| 2010/0228281 A1 | 9/2010 | Gilson et al. |
| 2011/0009943 A1 | 1/2011 | Paul et al. |
| 2011/0213403 A1* | 9/2011 | Aboytes ................ A61M 29/02 606/194 |
| 2011/0270178 A1 | 11/2011 | Fiorella et al. |
| 2011/0270298 A1 | 11/2011 | Abrams |
| 2011/0288572 A1 | 11/2011 | Martin |
| 2012/0059309 A1* | 3/2012 | di Palma ........... A61M 25/0074 604/509 |
| 2012/0083824 A1 | 4/2012 | Berrada et al. |
| 2012/0116351 A1 | 5/2012 | Chomas et al. |
| 2012/0316597 A1 | 12/2012 | Fitz et al. |
| 2013/0030461 A1* | 1/2013 | Marks ..................... A61F 2/013 606/200 |
| 2013/0110152 A1 | 5/2013 | Dubrul et al. |
| 2013/0144326 A1 | 6/2013 | Brady et al. |
| 2013/0310803 A1 | 11/2013 | Morsi |
| 2013/0317534 A1 | 11/2013 | Zhou et al. |
| 2013/0345739 A1 | 12/2013 | Brady et al. |
| 2014/0005712 A1 | 1/2014 | Martin |
| 2014/0039598 A1 | 2/2014 | Sampognaro et al. |
| 2014/0188156 A1 | 7/2014 | Tekulve et al. |
| 2014/0236219 A1 | 8/2014 | Dubrul et al. |
| 2014/0343602 A1 | 11/2014 | Cox et al. |
| 2015/0066075 A1 | 3/2015 | Russell et al. |
| 2015/0112376 A1 | 4/2015 | Molaei et al. |
| 2015/0190141 A1 | 7/2015 | Cragg et al. |
| 2015/0257775 A1 | 9/2015 | Gilvarry et al. |
| 2015/0343182 A1 | 12/2015 | Vazales et al. |
| 2015/0351770 A1 | 12/2015 | Fulton |
| 2015/0351775 A1 | 12/2015 | Fulton |
| 2016/0022293 A1 | 1/2016 | Dubrul et al. |
| 2016/0045202 A1 | 2/2016 | Ferry et al. |
| 2016/0058458 A1 | 3/2016 | Hansen et al. |
| 2016/0074024 A1 | 3/2016 | Scheule |
| 2019/0117244 A1 | 4/2019 | Wallace et al. |
| 2020/0345376 A1 | 11/2020 | Fulton, III |
| 2020/0368499 A1 | 11/2020 | Fulton, III |
| 2024/0050703 A1 | 2/2024 | Fulton, III |

FOREIGN PATENT DOCUMENTS

| | | |
|---|---|---|
| EP | 1179321 A2 | 2/2002 |
| EP | 1549229 A2 | 7/2005 |
| EP | 1617893 A1 | 1/2006 |
| EP | 1761298 A2 | 3/2007 |
| EP | 1799128 A2 | 6/2007 |
| EP | 1981413 A2 | 10/2008 |
| EP | 1399089 B1 | 12/2008 |
| EP | 1629784 B1 | 1/2010 |
| EP | 2057967 B1 | 1/2013 |
| EP | 2596828 A1 | 5/2013 |
| EP | 2683309 A2 | 1/2014 |
| EP | 2707077 A1 | 3/2014 |
| EP | 2744423 A1 | 6/2014 |
| EP | 2801325 A1 | 11/2014 |
| EP | 2854924 A1 | 4/2015 |
| EP | 2879625 A1 | 6/2015 |
| EP | 2908901 A2 | 8/2015 |
| EP | 2341845 B1 | 1/2016 |
| EP | 2979649 A1 | 2/2016 |
| FR | 2312264 A1 | 12/1976 |
| FR | 2380018 A1 | 9/1978 |
| GB | 2020557 A | 11/1979 |
| JP | H08308932 A | 11/1996 |
| JP | H10328306 A | 12/1998 |
| JP | 2006519657 A | 8/2006 |
| JP | 4731471 B2 | 7/2011 |
| JP | 5805736 B2 | 11/2015 |
| WO | WO-8001343 A1 | 6/1980 |
| WO | WO-8001353 A1 | 7/1980 |
| WO | WO-9424946 A1 | 11/1994 |
| WO | WO-9509024 A1 | 4/1995 |
| WO | WO-9516487 A1 | 6/1995 |
| WO | WO-9601591 A1 | 1/1996 |
| WO | WO-9923952 A1 | 5/1999 |
| WO | WO-9944506 A1 | 9/1999 |
| WO | WO-9944510 A1 | 9/1999 |
| WO | WO-9944542 A2 | 9/1999 |
| WO | WO-9944542 A3 | 11/1999 |
| WO | WO-0012009 A2 | 3/2000 |
| WO | WO-0012010 A1 | 3/2000 |
| WO | WO-0149208 A1 | 7/2001 |
| WO | WO-0197697 A1 | 12/2001 |
| WO | WO-02055146 A1 | 7/2002 |
| WO | WO-02087677 A2 | 11/2002 |
| WO | WO-03002028 A2 | 1/2003 |
| WO | WO-2004019791 A2 | 3/2004 |
| WO | WO-2004093966 A1 | 11/2004 |
| WO | WO-2005118050 A2 | 12/2005 |
| WO | WO-2006031410 A2 | 3/2006 |
| WO | WO-2007089897 A2 | 8/2007 |
| WO | WO-2008010197 A2 | 1/2008 |
| WO | WO-2008010197 A3 | 4/2008 |
| WO | WO-2008124567 A1 | 10/2008 |
| WO | WO-2010010545 A1 | 1/2010 |
| WO | WO-2012009675 A2 | 1/2012 |
| WO | WO-2012011518 A1 | 1/2012 |
| WO | WO-2012120490 A2 | 9/2012 |
| WO | WO-2012155093 A1 | 11/2012 |
| WO | WO-2013028579 A1 | 2/2013 |
| WO | WO-2013177383 A1 | 11/2013 |
| WO | WO-2014022409 A1 | 2/2014 |
| WO | WO-2014062645 A2 | 4/2014 |
| WO | WO-2014164535 A1 | 10/2014 |
| WO | WO-2014180702 A1 | 11/2014 |
| WO | WO-2015057796 A1 | 4/2015 |
| WO | WO-2015187196 A1 | 12/2015 |
| WO | WO-2016040923 A2 | 3/2016 |
| WO | WO-2016064077 A1 | 4/2016 |
| WO | WO-2017161204 A1 | 9/2017 |
| WO | WO2022251678 A1 | 12/2022 |

OTHER PUBLICATIONS

Final Office Action for U.S. Appl. No. 12/477,371 Mailed on Jun. 29, 2012.

Final Office Action for U.S. Appl. No. 12/477,371 Mailed on May 20, 2014.

Final Office Action for U.S. Appl. No. 13/725,871 Mailed on May 21, 2014.

International search report and written opinion dated Jul. 27, 2017 for PCT Application No. PCT/US2017/022837.

International search report and written report dated Apr. 21, 2015 for PCT Application No. PCT/US2014/067696.

International search report dated Oct. 15, 2004 for PCT Application No. PCT/US2004/011584.

Notice of allowance dated Apr. 20, 2017 for U.S. Appl. No. 14/645,830.

Notice of allowance dated Aug. 21, 2015 for U.S. Appl. No. 13/725,871.

Notice of Allowance dated Sep. 1, 2016 for U.S. Appl. No. 14/201,371.

Notice of allowance dated Dec. 12, 2000 for U.S. Appl. No. 09/189,574.

Office action dated Jan. 21, 2016 for U.S. Appl. No. 14/645,830.
Office action dated Feb. 25, 2015 for U.S. Appl. No. 13/190,416.
Office action dated Mar. 21, 2017 for U.S. Appl. No. 14/554,348.
Office Action dated Apr. 6, 2015 for U.S. Appl. No. 12/477,371.
Office action dated Apr. 6, 2015 for U.S. Appl. No. 13/725,871.
Office action dated Apr. 6, 2016 for U.S. Appl. No. 14/265,921.
Office action dated Apr. 9, 2014 for U.S. Appl. No. 13/190,416.
Office action dated Apr. 12, 2016 for U.S. Appl. No. 14/554,348.

(56) References Cited

OTHER PUBLICATIONS

Office action dated May 4, 2015 for U.S. Appl. No. 14/201,371.
Office action dated Jun. 6, 2000 for U.S. Appl. No. 09/189,574.
Office action dated Jun. 28, 2017 for U.S. Appl. No. 14/878,728.
Office action dated Jul. 17, 2017 for U.S. Appl. No. 14/645,830.
Office action dated Aug. 5, 2015 for U.S. Appl. No. 14/554,348.
Office action dated Aug. 5, 2015 for U.S. Appl. No. 14/645,830.
Office action dated Sep. 19, 2013 for U.S. Appl. No. 13/190,416.
Office action dated Oct. 8, 2014 for U.S. Appl. No. 13/190,416.
Office action dated Oct. 14, 1999 for U.S. Appl. No. 09/189,574.
Office Action dated Nov. 15, 2017 for U.S. Appl. No. 14/554,348.
Office action dated Nov. 20, 2014 for U.S. Appl. No. 14/201,371.
Office action dated Nov. 28, 2014 for U.S. Appl. No. 13/725,871.
Office Action for U.S. Appl. No. 10/747,813 mailed on Jan. 10, 2008. (6 pages).
Office Action for U.S. Appl. No. 10/747,813 Mailed on Jul. 26, 2007.
Office Action for U.S. Appl. No. 10/747,813 Mailed on Sep. 19, 2007.
Office Action for U.S. Appl. No. 10/765,564 Mailed Oct. 9, 2007.
Office Action for U.S. Appl. No. 10/866,980 Mailed on Oct. 5, 2007.
Office Action for U.S. Appl. No. 12/477,371 Mailed on Nov. 8, 2011.
Office Action for U.S. Appl. No. 12/477,371 Mailed on Sep. 27, 2013.
Office Action for U.S. Appl. No. 13/725,871 Mailed on Jul. 15, 2014.
Office Action for U.S. Appl. No. 13/725,871 Mailed on Sep. 5, 2013.
Schmitz-Rode, et al. New device for percutaneous fragmentation of pulmonary emboli. Radiology. Jul. 1991;180(1):135-7.
Sharafuddin, et al. Current status of percutaneous mechanical thrombectomy. Part I. General principles. J Vasc Interv Radiol. Nov.-Dec. 1997;8(6):911-21.
Supplementary European Search Report mailed Jul. 23, 2008 for EP Application No. 04759873.5, filed Apr. 15, 2004. (4 pages).
U.S. Appl. No. 14/554,348, filed Nov. 26, 2014.
U.S. Appl. No. 14/645,830, filed Mar. 12, 2015.
U.S. Appl. No. 14/645,830 Office Action dated May 3, 2018.
U.S. Appl. No. 14/878,728 Office Action dated Apr. 25, 2018.
Velocimed, "Proxis, Embolic Protection System", http://www.velocimed.com/proxis.htm (visited Feb. 5, 2004), (2003). (4 pages).
Notice of Allowance dated Sep. 28, 2016 for U.S. Appl. No. 13/190,416.
U.S. Appl. No. 14/878,728, filed Oct. 8, 2015.
U.S. Appl. No. 14/201,371 Office Action dated Nov. 9, 2015.
U.S. Appl. No. 14/554,348 Office Action dated Jun. 26, 2018.
U.S. Appl. No. 16/226,832 Notice of Allowance dated Nov. 4, 2021.

* cited by examiner

LOW RADIAL FORCE VASCULAR DEVICE AND METHOD OF OCCLUSION

CROSS-REFERENCE

This application is a continuation of U.S. patent application Ser. No. 16/226,832, filed Dec. 20, 2018, now U.S. Pat. No. 11,266,414; which is a continuation of U.S. application Ser. No. 14/554,348, filed on Nov. 26, 2014; which claims the benefit of U.S. Provisional Application No. 62/007,553, filed Jun. 4, 2014, which application is incorporated herein by reference.

BACKGROUND

Occlusive vascular disease is a common ailment in people resulting in enormous costs to the health care system and this cost is growing as the population ages. Many different endovascular devices have been developed to treat various segments and various conditions of this huge market. While many of these devices are quite effective at treating plaque, blood clots, occlusions, narrowing and the like, frequently they damage the blood vessel wall which incites an exuberant reparative effort by the body which results in a process termed restenosis. Restenosis is a secondary narrowing of the blood vessels caused by the injury to the blood vessel caused by the primary treatment.

Hence, there is a need for devices that successfully treat different conditions of the blood vessels but do not damage the vessel wall and incite the exuberant healing response that may result in restenosis, or secondary narrowing.

In some instances, it is necessary to temporarily occlude the blood vessel to deliver medicaments, to retrieve blood clot, to provide embolic protection, to anchor the catheter system, and the like. Balloon catheters are used frequently for these applications, but the outward radial force of the apparatus sufficient to produce occlusion may also be sufficient to damage the vessel wall enough to cause restenosis. A safe expansion of the balloon may be insufficient to arrest blood flow and blood may leak by the occluding member, which may propel medicaments, debris, and blood clot downstream to block smaller arteries. Too much radial force may damage the vessel wall enough to cause the restenosis cascade phenomenon, which is initiated by injury and damage to the smooth muscle cells in the media of the arterial wall, a well-known complication of balloon inflations. This cascade of events resulting in restenosis has been the "Achilles Heel" of vascular intervention as many interventions which distend the vessel, including angioplasty, stent placement, and balloon occlusion, damage the vessel wall as they attempt to correct a blockage, remove a clot, or the like. Generally, this complication should be avoided at all costs.

Balloons are notorious for causing damage to the vessel wall as they apply outward radial pressure that distends the blood vessel, injuring and damaging the blood vessel. The body's reparative effort comprises a complex series of events that results in exuberant scar tissue weeks to months later which cause the vessel to narrow significantly, a process known as "re-stenosis."

Hence, it is an object of the present disclosure to improve upon the current devices and provide blood flow occlusion in all predictable scenarios without causing damage to the blood vessel while doing so. To this end, devices and device features meeting at least some of these objectives discussed subsequently.

Additionally, improvements to other devices which may be utilized with occluding catheters as part of a system for thrombectomy, anchoring, embolic protection, vessel occlusion, drug delivery and other applications will be described.

SUMMARY

The present disclosure relates to medical systems, devices, and methods. More specifically, the present disclosure relates to systems, devices, and methods to treat diseased or stenosed blood vessels.

Devices, systems, and methods are disclosed for occluding a blood vessel and/or capturing a blood clot or thrombus within. An occlusion apparatus may comprise inner and outer sheaths and an expandable flexible tubular sleeve. The occlusion apparatus may be advanced to a target site in the blood vessel. A dilator having a soft, compressible tip may be advanced through a lumen of the inner sheath to facilitate the advancement of the occlusion apparatus. The sheaths may be translated relative to one another to expand the flexible tubular sleeve to a funnel shape with a distal flush portion contacting the blood vessel inner wall and a proximal tapered portion. The proximal portion may be fluid permeable so that blood can pass through to apply pressure on the vessel wall through the distal portion. A capture device and/or a traction device can be advanced out of the inner sheath lumen and retracted back therein to capture thrombus. The distal portion of the device may comprise an expandable mesh braid with a memory characteristic to limit expansion.

Aspects of the present disclosure may also be directed to a funnel catheter comprising an outer tube, an inner tube slidably located within the outer tube, and a tubular sleeve having first and second ends and movable between a radially expanded, use state and a radially contracted, deployment state. The first end of the sleeve may be secured to a distal end of the outer tube. The second end of the sleeve may be secured to a distal end of the inner tube. The sleeve may have a movable, generally U-shaped direction-reversing region so that when the first and second ends move relative to one another, the position of the direction-reversing region may move relative to the distal ends of the inner and outer tubes. The direction-reversing region may comprise the distal funnel catheter end. The sleeve may be comprised of an elastomeric coating applied or covering a part of the sleeve and a part of the sleeve which may not have an elastomeric covering.

Aspects of the present disclosure may also be directed to a method for deploying a material-directing element within a tubular structure within a patient. A funnel catheter, having a distal funnel catheter end, may be selected. The funnel catheter may comprise an outer tube, an inner tube slidably located within the outer tube, and a tubular sleeve having first and second ends and movable between a radially expanded, use state and a radially contracted, deployment state. The first end of the sleeve may be secured to a distal end of the outer tube. The second end of the sleeve may be secured to a distal end of the inner tube. The sleeve may have a movable, generally U-shaped direction-reversing region, which may comprise the distal funnel catheter end. The funnel catheter may be deployed with the sleeve in the reduced diameter, deployment state and with the sleeve being generally parallel to the outer and inner tubes. The direction-reversing region may be positioned at a chosen position within a tubular structure within a patient. The distal ends of the inner and outer tubes may be moved relative to one another to cause: the position of the direction-reversing region to move relative to the first and second ends, the sleeve to form a distally-opening material-directing funnel, and the distal funnel portion to contact the inner wall of the tubular structure. The funnel may have a distal funnel portion and a proximal funnel portion. The distal funnel portion may comprise an elastomeric covering and the proximal portion may not be comprised of an elastomeric coating.

Aspects of the present disclosure may also be directed to an improved traction device which may be placed coaxially through the funnel catheters described herein. The improved traction device may comprise an outer sleeve and inner member placed coaxially within the outer sleeve. Both the sleeve and the inner member may have proximal and distal ends. The distal end of the outer sleeve may be attached to the proximal end of a length of a deformable tubular braid. The distal end of the inner member may be attached to the distal end of the length of the deformable tubular braid. When the inner member is moved proximally relative to the outer sleeve, the deformable tubular braid may contract so that the ends of the deformable tubular braid are positioned closer together and the waist of the tubular braid expands. The traction device can include further features described herein that are directed to the ease of use and more efficient function amongst other improvements. Prior traction devices are described in U.S. Pat. Nos. 6,238,412 and 6,699,260, issued to the current inventor as a co-inventor.

Aspects of the present disclosure may also be directed to occlusion apparatuses for occluding a bodily vessel. An occlusion apparatus may comprise an outer sheath, an inner sheath, and a flexible tubular sleeve having a contracted configuration and an expanded configuration. The outer sheath and the inner sheath may be translatable relative to one another to actuate the flexible tubular sleeve between the contracted and expanded configurations. The flexible tubular sleeve in the expanded configuration may have a funnel shape with a distal flush portion adapted to contact an inner wall of the bodily vessel when the flexible tubular sleeve is expanded therein and a proximal tapered portion. At least a part of the proximal tapered portion may be fluid permeable such that bodily fluid within the bodily vessel can pass through the fluid permeable part to apply pressure on the inner wall of the bodily vessel through the distal flush portion. The bodily vessel will typically comprise a blood vessel and the bodily fluid within the bodily vessel will typically be blood. The occlusion apparatus, however, may also be used with other bodily vessels such as bile ducts, esophagus, fallopian tubes, urethra, and intestines.

The inner sheath may be disposed at least partially within the outer sheath. The flexible tubular sleeve may have a first end and a second end. The first end may be coupled to a distal end of inner sheath and/or the second end may be coupled to a distal end of the outer sheath. The distal end of the inner sleeve may be distal of the distal end of the outer sleeve when the flexible tubular sleeve is in the contracted configuration. The flexible tubular sleeve may be biased to assume the expanded configuration with the funnel shape. For example, the flexible tubular sleeve comprises a shape memory material such as Nitinol. The shape memory material may be fashioned in a way to be biased to assume the funnel shape as described below.

At least a part of the distal flush portion may be fluid impermeable. The fluid impermeable part of the distal flush portion may be distal of the fluid permeable part of the proximal tapered portion when the flexible tubular sleeve is in the expanded configuration. The fluid impermeable part of the distal flush portion and/the fluid permeable part of the proximal tapered portion may extend over at least a full circumference of the flexible tubular sleeve. The fluid impermeable part of the distal flush portion may comprise an elastomeric covering.

The flexible tubular sleeve may comprise a mesh braid. The flexible tubular sleeve may comprise a U-shaped direction-reversing region adapted to move relative to one or more of the inner and outer sheaths as the inner and outer sheaths are translated relative to one another. The U-shaped direction-reversing region may be disposed at a distal end of the flexible tubular sleeve. The distal flush portion of the flexible tubular sleeve in the expanded configuration may be adapted to apply a radially outward force sufficient to occlude fluid flow in the bodily vessel.

Aspects of the present disclosure may also be directed to systems for treating a disease within a bodily vessel. A system may comprise any of the occlusion apparatuses described herein. The system may further comprise a dilator advanceable at least partially through a lumen of the inner sheath of the occlusion apparatus so that a distal tip of the dilator is distal of the occlusion apparatus. The dilator may have a malleable and oversized distal tip with a greater cross-sectional area than a distal tip of the inner sheath of the occlusion apparatus. Alternatively or in combination, the system may further comprise a traction apparatus translatable at least partially through the lumen of the inner sheath so that an expandable mesh braid on a distal portion of the traction apparatus can be positioned and expanded distal of the occlusion apparatus.

The dilator and/or traction apparatus may have a guidewire lumen. Retraction of one or more of the dilator and/or traction apparatus when advanced distally past the occlusion apparatus can capture and retract material in the bodily vessel into the lumen of the inner sheath. The expandable mesh braid of the traction apparatus may be configured to apply a predetermined limited amount of radially outward force when expanded in the bodily vessel and elongate to minimize distending or damaging the bodily vessel as the expandable mesh braid is expanded. The bodily vessel will typically comprise a blood vessel and the bodily fluid within the bodily vessel will typically be blood. The occlusion apparatus, however, may also be used with other bodily vessels such as bile ducts, esophagus, fallopian tubes, urethra, and intestines.

Aspects of the present disclosure may also be directed to methods of treating a bodily vessel. A method may comprise the steps of advancing an occlusion apparatus to a target site in a bodily vessel and expanding a flexible tubular sleeve of the occlusion apparatus to a funnel shaped expanded configuration occluding the bodily vessel at the target site. A distal flush portion of the flexible tubular sleeve may contact an inner wall of the bodily vessel when expanded. A proximal tapered portion of the flexible tubular sleeve may allow bodily fluid within the bodily vessel to pass at least partially therethrough to apply pressure on the inner wall of the bodily vessel through the distal flush portion.

At least a part of the distal flush portion may be fluid impermeable and at least a part of the proximal tapered portion may be fluid permeable. To expand the flexible tubular sleeve, an inner sheath and an outer sheath of the occlusion apparatus may be translated relative to one another. Such translation can move a U-shaped direction reversing region of the flexible tubular sleeve relative to one or more of the inner or outer sheaths. The distal flush portion of the flexible tubular sleeve in the expanded configuration may be adapted to apply a radially outward force sufficient to occlude fluid flow in the bodily vessel. This radially outward force may be from a combination of the inherent structure of the expanded flexible tubular sleeve and the pressure from the bodily fluid passed through the proximal tapered portion. The flexible tubular sleeve may be biased to assume the funnel shaped expanded configuration. Expanding the flexible tubular sleeve may comprise allowing the flexible tubular sleeve to assume the funnel shaped expanded configuration.

The occlusion apparatus may be advanced over a guide wire. The method may further comprise advancing a dilator through the occlusion apparatus. The dilator may be advanced through a distal end of the occlusion apparatus. The dilator may further be retracted within the bodily vessel to capture and retract material in the bodily vessel into an inner lumen of the occlusion apparatus. The material captured and retracted may comprise a clot or a thrombus. The dilator may have a malleable and oversized distal tip having a greater cross-sectional area than a distal tip of the inner sheath of the occlusion apparatus.

The method may further comprise a step of advancing a traction apparatus through the occlusion apparatus. The traction apparatus may have an expandable mesh braid on a distal portion thereof. The traction apparatus may be advanced through a distal end of the occlusion apparatus. The method may further comprise a step of expanding the expandable mesh braid to appose the inner wall of the bodily vessel. The expanded expandable mesh braid may be configured to apply a limited radially outward force when expanded in the bodily vessel and elongate to minimize distending or damaging the bodily vessel as the tubular outer sleeve is expanded. The expandable mesh braid may comprise a plurality of wires configured to exert a maximum predetermined outward radial force when the expandable mesh braid is in the expanded configuration. The method may further comprise a step of retracting the expanded expandable mesh braid within the bodily vessel to capture and retract material in the bodily vessel into an inner lumen of the occlusion apparatus. The material captured and retracted may comprise a clot or a thrombus.

Expanding the flexible tubular sleeve of the occlusion apparatus to the funnel shaped expanded configuration may apply a radially outward force from the expanded flexible tubular sleeve to hold the flexible tubular sleeve in place in the bodily vessel. The radially outward force may comprise blood pressure transmitted through the expanded flexible tubular sleeve and an inherent radially outward force from the expanded flexible tubular sleeve. The radially outward force mostly may comprise the blood pressure transmitted through the expanded flexible tubular sleeve. The radially outward force may be transmitted from blood passing through at least a portion of the flexible tubular sleeve.

Aspects of the present disclosure may also be directed to devices for dilating a bodily vessel. The device may comprise a shaft and a malleable and oversized distal tip coupled to the shaft. The shaft may have an inner lumen for the passage of a guidewire and may be advanceable through a catheter lumen. The malleable and oversized distal tip may be coupled to the shaft and may have a cross-sectional area greater than that of the shaft. The oversized distal tip may be compressible to be advanceable through the catheter lumen. The malleable and oversized distal tip may comprise a first material and the shaft may comprise a second material, the first material having a softer durometer than the second material. The malleable and oversized distal tip may have a radial cut-out to provide compressibility. Typically, the bodily vessel will be a blood vessel but the dilator devices may be used for other bodily vessels as well.

Aspects of the present disclosure may also be directed to methods for dilating a bodily vessel. The method may comprise the steps of positioning a dilator within a lumen of a catheter such that an oversized distal tip of the dilator is advanced out of the catheter lumen and decompresses and advancing the oversized distal tip of the dilator and the catheter to a target site. Typically, the bodily vessel will be a blood vessel but the dilator devices may be used for other bodily vessels as well. The target object will typically comprise a blood clot or a thrombus. The catheter may comprise an occlusion catheter, and may further comprise expanding the occlusion catheter at the target site to occlude the target site. The method may further comprise a step of retracting the oversized distal tip of the dilator to capture a target object at the target site at least partially within an expanded tubular sleeve of the occlusion catheter and/or the lumen of the catheter. The oversized distal tip of the dilator may have a greater cross-sectional area than that of a shaft of the dilator the oversized distal tip is coupled to.

Aspects of the present disclosure may also be directed to traction apparatuses for treating a bodily vessel. A, traction apparatus may comprise an inner shaft having a distal end, a tubular outer sleeve coaxially disposed over the inner shaft and having a distal end, and an expandable mesh braid coaxially disposed over the inner shaft and coupled to the distal ends of the inner shaft and the tubular outer sleeve. The inner shaft and the tubular outer sleeve may be translatable relative to one another to shift the expandable mesh braid between contracted and expanded configurations. The expandable mesh braid may be configured to apply a predetermined maximum amount of radially outward force when expanded in the bodily vessel and to elongate to minimize distending or damaging the bodily vessel as the tubular outer sleeve is expanded.

The mesh braid may comprise a plurality of wires. The plurality of wires may have been treated to provide a combination of stiffness and flexibility so that the expandable mesh braid applies the predetermined maximum amount of radially outward force when expanded in the bodily vessel and elongates to minimize distending or damaging the bodily vessel as the tubular outer sleeve is expanded. The plurality of wires may comprise a plurality of Nitinol wires. The plurality of wires may have been heat treated. The plurality of wires may be configured to exert the predetermined maximum amount of radially outward force when the expandable mesh braid is in the expanded configuration. The plurality of wires may be configured to exert the predetermined maximum amount of radially outward force independently of the inner diameter of the bodily vessel.

The expandable mesh braid in the expanded configuration may be configured to expand to appose an inner wall of the bodily vessel while minimizing resultant expansion of the bodily vessel. The expandable mesh braid may be expandable to a maximum predetermined outer diameter to apply the predetermined maximum amount of radially outward force. The expandable mesh braid may have a shape memory characteristic to limit expansion of the expandable mesh braid to the maximum predetermined outer diameter. Further translation of the inner shaft and the tubular outer sleeve relative to one another after the expandable mesh braid has been expanded to the maximum predetermined outer diameter may axially lengthen an outer surface of the expandable mesh braid. That is, a degree of translation of the inner shaft and the tubular outer sleeve relative to one another may have a non-linear relationship(s) with an outer diameter of the expandable mesh braid and/or a radially outward pressure exerted by the expandable mesh braid. The expandable mesh braid may have a permeable portion to allow fluid within the bodily vessel to enter an interior of the expandable mesh braid and may apply radially outward pressure on the bodily vessel through an impermeable portion of the expandable mesh braid. Typically, the bodily vessel comprises a blood vessel.

Aspects of the present disclosure may also be directed to methods of treating a bodily vessel. A catheter may be introduced to a target site in the bodily vessel. A traction apparatus from within an inner lumen of the catheter may be advanced to position an expandable mesh braid of the traction apparatus. The expandable mesh braid may be expanded within the target site. The expanded mesh braid may be retracted to capture and retract material in the target site into the inner lumen of the catheter. The bodily vessel will typically comprise a blood vessel. The captured and retracted material may comprise a blood clot or a thrombus.

To expand the expandable mesh braid, an outer surface of the expandable mesh braid may be apposed against an inner wall of the bodily vessel. The expandable mesh braid may be configured to apply a predetermined maximum amount of radially outward force when expanded in the bodily vessel and to elongate to minimize distending or damaging the bodily vessel as the tubular outer sleeve is expanded. The expandable mesh braid may comprise a plurality of wires configured to exert the predetermined maximum amount of radially outward force when the expandable mesh braid is in the expanded configuration. The plurality of wires may be configured to exert the predetermined maximum amount of radially outward force independently of the inner diameter of the bodily vessel. The expandable mesh braid in the expanded configuration may be configured to expand to appose an inner wall of the bodily vessel while minimizing resultant expansion of the bodily vessel.

The expandable mesh braid may be expanded to a maximum predetermined outer diameter. The expandable mesh braid may have a shape memory characteristic to limit expansion of the expandable mesh braid to the maximum predetermined outer diameter. To expand the expandable mesh braid, an inner shaft and a tubular outer sleeve of the traction apparatus may be translated relative to one another. Further translation of the inner shaft and the tubular outer sleeve relative to one another after the expandable mesh braid has been expanded to the maximum predetermined outer diameter may axially lengthen an outer surface of the expandable mesh braid. That is, a degree of translation of the inner shaft and the tubular outer sleeve relative to one another may have a non-linear relationship(s) with an outer diameter of the expandable mesh braid and/or a radially outward pressure exerted by the expandable mesh braid.

To expand the expandable mesh braid, fluid within the bodily vessel may be allowed to enter an interior of the expandable mesh braid and apply radially outward pressure on the bodily vessel through the expandable mesh braid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

DETAILED DESCRIPTION

There is a continuing need for improved medical devices and methods to meet some or all the following objectives.

An objective may be to reduce cost. Cost reduction may be particularly important in recent years where it is clear for safety and sanitary reasons that many devices used in the vasculature should be single use devices. Devices, even if performing a function in some improved manner, will not be widely used if they are considerably more costly than the alternatives available.

Another objective may be ease of use and simplicity of understanding. Ease of use and simplicity can encourage device adoption and use by medical personnel. They can also tend to keep cost low.

Another objective may be to provide devices that entail procedures with which the medical profession is already familiar. By doing so, the skills that have been learned from previous experience can continue to have applicability.

Another objective relates to the effectiveness and thoroughness with which the device performs, such as blockage removal and vessel occlusion. For example, it is generally important that a maximum amount of the blockage be removed, recognizing that no device is likely to provide one hundred percent removal.

Another objective concerns safety—a matter, which is often so critical as to trump the other considerations. It is generally important to avoid tissue trauma. In many circumstances, it is critically important to, for example, avoid breaking up a blockage in a fashion that leads to flushing elements of the blockage throughout the body such as by damaging the blood vessels by applying excess pressure on the vessel wall in an attempt to fully occlude the vessel so that blockages can be removed and debris can be prevented from flushing downstream. A goal of the devices disclosed herein is to do just that: provide effective occlusion of a blood vessel to remove blockages and prevent debris from flushing downstream in a manner which does not damage the vessel wall in doing so.

There are often trade-offs in design considerations to achieve the above interrelated objectives. Extreme simplicity and a very simple procedure might over compromise safety. Addressing all of these considerations often calls for some trade-off between the objectives while maintaining the effectiveness and doing so safely.

Figure 1:
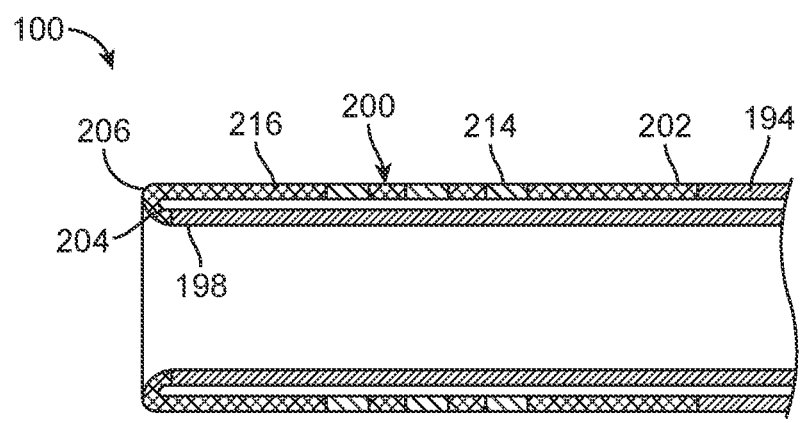
FIG. 1 illustrates a side view of a prior funnel catheter with its funnel element contracted.

FIG. 1 is an illustration of a prior art occlusion device or funnel catheter 100 in which the proximal end 202 of the tubular mesh braid 200 is attached to the distal aspect of the outer sleeve 194 and the distal end 204 of the tubular mesh braid 200 is attached to the distal aspect 198 of the inner sleeve 196. In the contracted or non-deployed configuration, as illustrated in FIG. 1, the tubular mesh braid 200 covers the distal aspect 196 of the inner sleeve 196. The catheter 100 is essentially in a typical configuration of a standard catheter, albeit with an outer sleeve 194 and inner sleeve 196 comprising the catheter wall. An impervious coating 216 covers the tubular mesh braid 200, but there may be areas of various porosity 214 in which there is no membrane which serves to enhance the expansile characteristics of the braid 200 by providing areas that are not restricted from expanding because of the elastomer.

Figure 2:
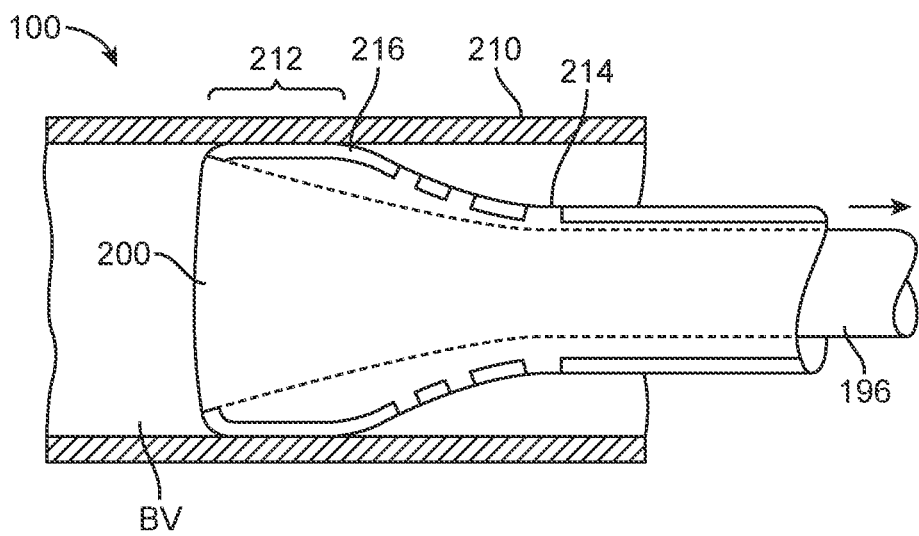
FIG. 2 illustrates a side view of the prior funnel catheter of FIG. 1 with its funnel element expanded.

FIG. 2 is an illustration of a prior art device 100 placed into a blood vessel BV and with the inner sleeve 196 withdrawn. Withdrawal of the inner sleeve 196 may cause the flexible tubular mesh braid 200 to buckle in a predetermined manner because of the manner in which the tubular mesh braid 200 was formed so that the tubular mesh braid 200 creates a funnel shape on the distal catheter. The margins of the funnel tip expand to contact the blood vessel wall 210 with a predetermined amount of radial force to occlude blood flow. The length 212 of the wall contact of the margin of the tubular mesh braid 200 may also be important in assisting the occlusion of blood flow. As well, the tubular mesh braid 200 may comprise a coating or a membrane 216 that is essentially impervious to blood but may comprise a variable porosity region 215 in a portion of the braid. This variable porosity region 215 can allow some fluid communication to the space between the inner and outer portions of the tubular mesh braid 200 when the tubular mesh braid is deployed in a funnel shape and can assist in the expansion of the tubular braid as there is less elastomer on the braid, hence less restriction to expansion. The variable porosity may also prevent a vacuum from forming within the folded more or less impervious braid that may prevent it from expanding correctly into a funnel shape.

However, in cases with an exaggerated systolic blood pressure of 160 mm Hg or in a larger vessel with exaggerated flow such as the carotid or renal arteries, the outward radial force and the length of braid contacting the vessel wall may not be sufficient to arrest the blood flow on a consistent basis. By providing an outward radial force adequate to arrest blood flow, the outward radial force may cause compression of the vessel wall 210, damaging the wall 210 similar to the forces exerted by balloon inflation which is known to damage the wall and result in restenosis. Hence, there may be a need for improved occlusion devices which do arrest blood flow in cases of exaggerated systolic blood pressure or exaggerated high flow states on a consistent and reliable basis, but without exerting an undue or exaggerated amount of force on the vessel wall to do so.

Moreover, there may be a dilemma with utilizing an outward radial force as the primary means of arresting blood flow as the optimal radial force to arrest blood flow varies as the optimal amount or size of the expanded funnel tip to arrest flow may vary in different sized vessels. The radial force and the size of the funnel tip will be different in a 2 mm coronary artery than in a 6 mm carotid artery and even still different in a 9 mm iliac artery. Hence, for different sized vessels, arresting the flow may demand the use of funnel tips with different sizes and different radial forces and different length of the wall contacting surface of the tubular mesh braid 200. This need for different sizes may create a situation in which it may be difficult to arrest flow over a continuum of sizes and flow situations, which can occur within a single vascular distribution as is the case in the lower extremity, with one design and one size of funnel tip. With the prior art occlusion device 100, while the funnel tip may oppose and contact the wall over a spectrum of sizes, the ability to occlude over this spectrum of sizes may be limited and may necessitate funnel tips sized specifically for the vessel size. The radial pressure exerted on a 2 mm diameter vessel will be greater than the radial pressure exerted on a 6 or 9 mm diameter vessel. As well, because of the different blood pressures in different patients and different flow rates in different arteries within the same patient, devices should be constructed to provide a greater force than is typically needed so to address the worst possible case which is elevated blood pressure and flow although most cases would not demand it. Hence, there may be a need for improved occlusion devices which do arrest blood flow over a range of vessel sizes with an optimized funnel tip which provides radial force sufficient to contact the wall but insufficient radial force to damage the wall. Meeting these needs can be accomplished by adding one or more features to the prior art occlusion device to improve upon it so that the occlusion device will arrest flow in cases of exaggerated systolic blood pressure, exaggerated high flow, and over a range of different sized arteries.

The sealing or occlusion efficiency of the prior art device can be summarized by the formula:

Occlusion efficiency of prior art occlusion device=radial force of braid*length or area of contact.

Hence, the longer the length (greater area of contact), the less radial force may be needed to occlude.

Figure 3:
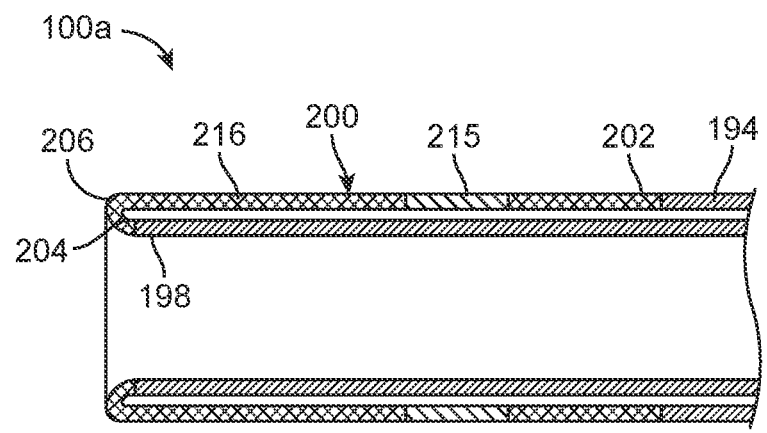
FIG. 3 illustrates a side view of an occlusion or funnel catheter with its funnel or braid element contracted and with a distinct portion of the funnel or braid element not covered by a membrane, according to some embodiments.
Figure 4:
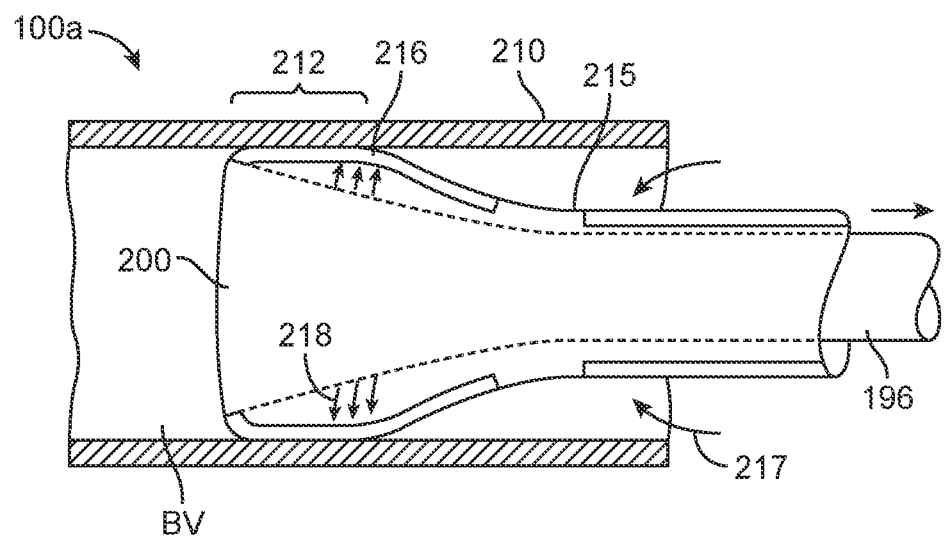
FIG. 4 illustrates a side view of the occlusion or funnel catheter of FIG. 3 with its funnel or braid element in its expanded, funnel shaped configuration with a distinct portion of the funnel or braid element covered by a membrane and a distinct portion not covered by a membrane.

FIG. 3 is an illustration of an occlusion device or funnel catheter 100a in accordance with embodiments of the present disclosure in an undeployed or contracted configuration. FIG. 4 is an illustration of the same occlusion device 100a in a deployed or expanded configuration in the blood vessel BV. The occlusion device 100a can solve the problem of the prior art occlusion device 100 and can arrest blood flow completely irrespective of the systolic blood pressure or the amount of flow within the vessel. The occlusion device 100*a* may comprise a catheter with an inner sleeve 196, an outer sleeve 194, and a length of tubular mesh braid 200 in which the proximal end 202 of the tubular mesh braid 200 is attached to the distal aspect of the outer sleeve 194 and the distal end 204 of the tubular mesh braid 200 is attached to the distal aspect of the inner sleeve 196. As with the prior art occlusion device 100, the occlusion device 100*a* may be constructed so that the funnel tip contacts the vessel wall location 212 with a radial or outward force and with a length of contact with the vessel wall location 212 sufficient to arrest blood flow in most instances.

In addition to the two features present in the prior art device 100 to occlude flow, the current occlusion device 100*a* also comprises a distinct coating or membrane free portion 215 of the tubular mesh braid 200 in addition to the coated or membrane containing section 216. Fluid or blood may flow freely though this coating free or membrane free section 215 of the tubular mesh braid, as indicated by the arrows 217, and by doing so will enhance the expansion of the wall contacting segment 212 of the tubular mesh braid 217 by adding the transmitted blood pressure to the outward or radial force of the funnel tip as demonstrated by the arrows 218 so that a seal is achieved no matter the systolic blood pressure, flow state of the vessel or the size of the vessel. The transmitted blood pressure may be additive to the inherent radial outward force utilized to expand a significant length of the funnel tip against the wall as the transmitted blood pressure essentially presses the impervious portion of the tubular mesh braid against the vessel wall. This added pressure can be summarized by the formula:

Occlusion efficiency of current occlusion device=radial force of braid*area of contact+ nominal transmitted blood pressure*area of contact Hence, the sealing ability of the current occlusion device 100*a* can be a reflection of a combination of the radial force of the braid, the length of the impervious wall contact portion, and the transmitted blood pressure. It can be important to recognize that the coating or membrane free or open portion of the tubular mesh braid 200 should be sized so that a portion of the coated or membrane comprising the impervious portion of the tubular mesh braid 200 is not compromised and that the length of contact of this portion to the wall is maximized while also providing a distinct segment of the tubular mesh braid 200 that allows ingress and egress of fluid or blood. Experiments have demonstrated that the optimal length of the open or membrane devoid portion is between 30-40% of the entire length of the tubular mesh braid 200 to accommodate a wide range of vessel sizes, although the ranges could vary between 20-60% and even 3-80% for different or specific situations. Actual overall braid length optimally for 2-6 mm vessels may be 1.6 cm with the coated or membrane containing section comprising 1.1 cm and the membrane or coating devoid portion comprising 0.5 cm. In larger vessels, the measurement may increase, but the approximate ratios will remain. This optimized length provides proper buckling of the braid 200 to form a funnel, proper ingress and egress of fluid so that the funnel tip expands and contracts easily, promptly, and without difficulty and also provides enough length of contact with the vessel wall so that the device occludes flow in any situation.

Because of the addition of these important features of providing an optimized section of the braid which does not comprise a membrane or coating to the prior art, the current devices can function consistently to arrest blood flow in blood vessels no matter the blood vessel size, the systolic blood pressure or the flow state of the vessel. As the systolic blood pressure is elevated, a corresponding pressure increase can be transmitted to the inside of the elastomeric coated braid through this section of uncoated braid to press it against the arterial wall insuring a proper seal and occlusion over varying blood pressures.

Experiments have demonstrated that the present occlusion device 100*a* can provide a nominal radial force against the blood vessel wall which is significantly augmented by the contribution of the patient's own blood pressure which is transmitted through the specific section of the braid 200 which is devoid of a membrane or coating. A 1.6 cm tubular mesh braid was constructed with 0.005" diameter Nitinol wire and bonded to inner and outer tubular catheters and a silicone elastomer was applied over 1.1 cm of length maintaining a 0.5 cm length devoid of the elastomer. This arrangement caused the braid to buckle properly and form a funnel shape when the inner and outer catheter members were translated relative to one another. Compressive unloading measurements, which are reflective of the outward radial force of the device, were performed and the results are presented in the table shown by FIG. 10.

Figure 10:
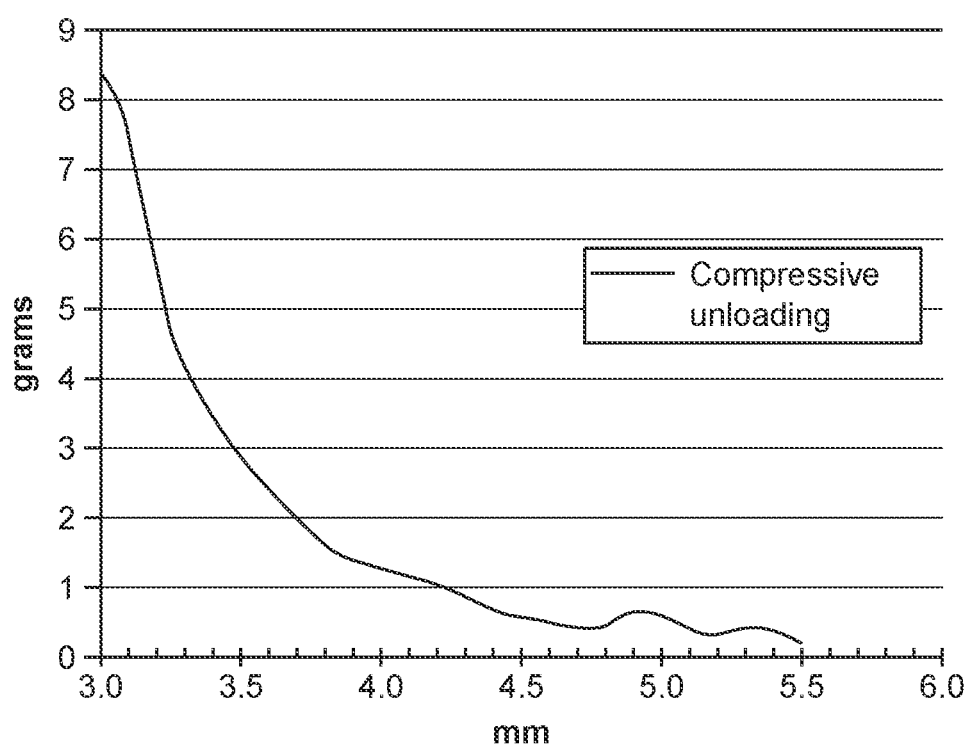
FIG. 10 shows a graph of compressive unloading for the experimental occlusion or funnel catheter of FIGS. 3 and 4, according to some embodiments.

The FIG. 10 graph demonstrates that the current occlusion device 100*a*, as constructed, may exert only a very nominal pressure against the vessel wall which is insufficient to damage the intima or media of the blood vessel. To create an occlusion of the vessel, however, the force exerted against the wall location 212 should be greater than the systolic blood pressure or there may be an incomplete seal and leakage of blood around the device. The current device 100*a*, because of the combination of structural features, can achieve an outward radial force greater than the patient's systolic blood pressure by providing a minimal amount of inherent outward radial force insufficient to damage the vessel wall added to the patient's transmitted systolic blood pressure and it can do so relatively independently of the diameter of a blood vessel, as demonstrated in the graph. Hence, over a range of sizes, a consistent and balanced limited inherent outward radial pressure can be achieved.

Calculations reveal that a systolic blood pressure of 150 mm Hg would demand at least 285 grams of outward radial pressure from a balloon or even the prior art funnel catheter to occlude a blood vessel. At this level, a segment of the arterial wall adjacent to the upstream balloon face may experience 570 grams of force as there would be at least 285 grams of outward radial force provided by the balloon and 285 grams from the 150 mm Hg blood pressure. This may be enough to damage the vessel wall and create immediate or delayed complications. The occlusion devices of the present disclosure may subject the vessel wall to only 285 grams from the transmitted blood pressure (which it is adapted to withstand) and 1.4 grams from the inherent outward radial force of the devices. Hence, the occlusion devices of the present disclosure may add only 0.5% added pressure to the wall over the transmitted blood pressure whereas a balloon or even the prior art funnel catheter needs 100% added pressure to occlude. Hence, the occlusion devices of the present disclosure may be dramatic improvements in safety over prior art devices as vessel occlusion can be accomplished over a wide range of vessel sizes, flow rates and blood pressures by exerting a very minimal outward radial pressure on the vessel wall which is insufficient to damage to the vessel wall.

By providing a membrane devoid section of braid 200 through which the blood may flow into the space between the inner shaft 196 of the device 100*a* and the membrane containing braid 200, the total force of the device will generally always exceed the patient's systolic blood pressure. The systolic blood pressure will often be exceeded by the inherent outward radial force of the braid 200 (which is less than one gram in many instances) as the outward radial force of the braid 200 and the transmitted systolic blood pressure will often combine to press the membrane containing segment of the braid against the vessel wall preventing any leakage of blood around the device 100*a*.

To create a section of tubular braid 200 with portions that are impervious to flow and other portions in which fluid and blood may flow freely though, there may be several different methods available. Dip coating is one very practical method to apply the elastomer to the braid 200 and the braid 200 may be dipped into a solution of the elastomer just enough to make part of the section of tubular braid 200 impervious to fluids leaving the non-dipped portion free of the elastomer. Such dip coating can be somewhat inexact and tedious however. It may be appropriate to dip the entire section of tubular mesh braid 200 into the elastomer or coat the entire section in some other manner and then laser cut the elastomer from the intended porous portion of the braid 200. This latter method can be more exact and precise and can leave a portion of the tubular braided section 200 with an elastomeric membrane or coating and part of the section with no elastomer and freely porous. There are other means known in the art of creating porous and non-porous sections of tubular braid.

Figure 11:
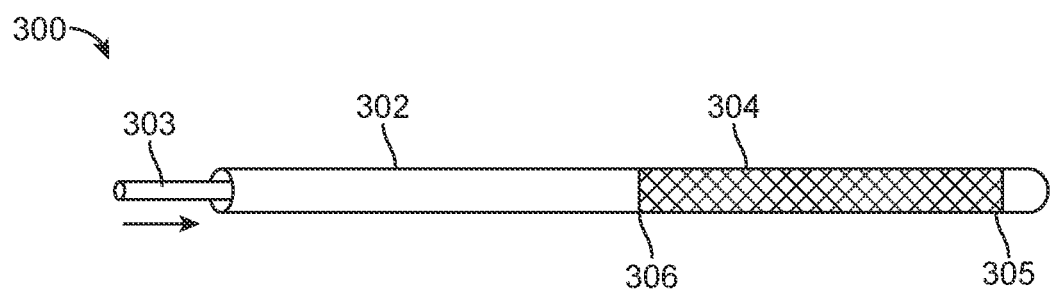
FIG. 11 shows a side view of a prior traction device in its contracted, delivery configuration.

In some cases, it may be advantageous to provide another device to propel a blood clot or other substance into the mouth of a catheter or even to expand to serve as a filter or an additional occlusion device. This may include a device to engage the blood clot and pull it toward the catheter mouth or opening. Prior art traction devices include balloon catheters, which are known to damage the vessel wall when fully expanded, and braided devices such as described in my prior U.S. Pat. No. 6,635,068, entitled "Occlusion, Anchoring, Tensioning and Flow Direction Apparatus and Methods for Use." Even the latter prior art traction device may damage the vessel wall in at least some cases by a combination of the outward radial force and the irregular surface caused by the braid. A prior art traction device 300 is illustrated in FIG. 11 comprising a tubular outer sleeve 302 coaxially containing or over an inner member or shaft 303. An inner member 303 is attached to the distal end of the annular braid 304 at location 305. The outer sleeve 302 is attached to the annular braid 304 at location 306. FIG. 11 shows the configuration in which the device 300 is inserted into the blood vessel BV.

Figure 12:
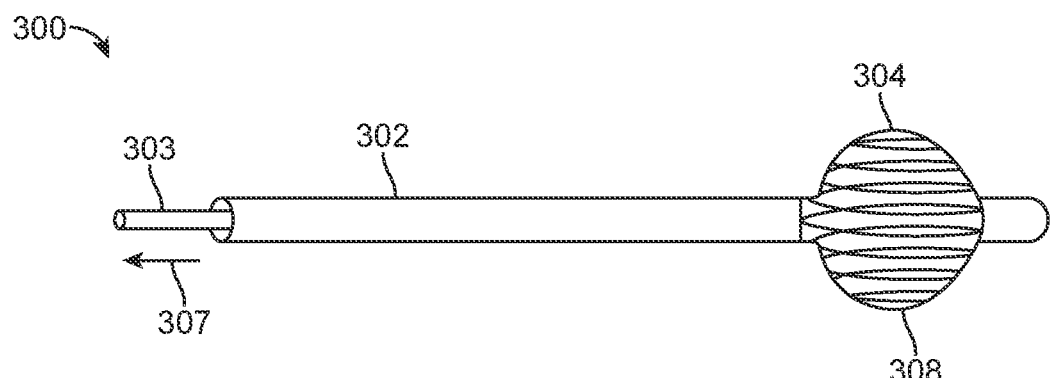
FIG. 12 show a side view of the traction device of FIG. 11 in its expanded configuration.

FIG. 12 demonstrates the configuration utilized for the functioning of the traction device 300, whether as a traction device on a thrombus or embolus, a filter device, or a tensioning device. The inner member 303 may be moved relative to the outer sleeve 302 as indicated by the arrow 307. This relative motion can cause the annular braid 304 to expand radially as shown at location 308. Typically, the inner shaft of this device 300 is translated proximally relative to the outer shaft causing the braid to expand in a more or less linear relationship to the degree of translation. The materials and construction of the braid for this traction device 300 may be chosen to increase the degree of outward radial force to insure anchoring, tensioning, and occlusion and to maximize the outward radial force.

Figure 13:
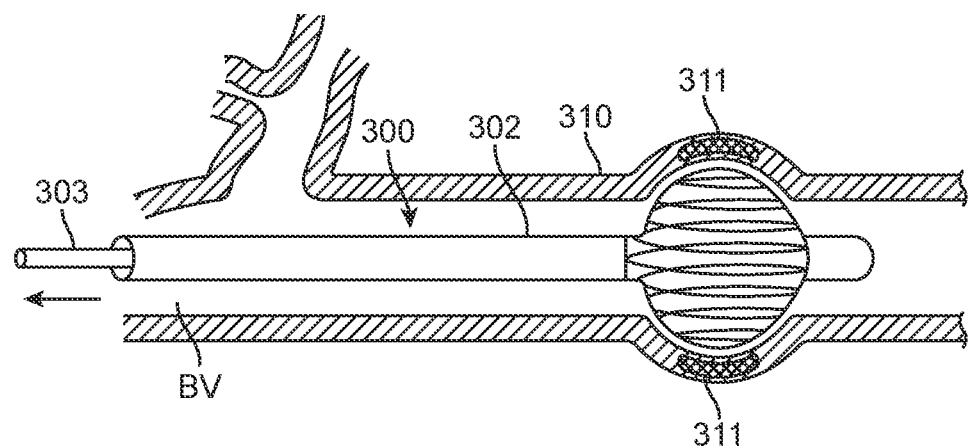
FIG. 13 shows a side view of the traction device of FIG. 11 expanded in a blood vessel.

As demonstrated in FIG. 13, the wall 310 of the blood vessel BV may be expanded by the expansion of the wire basket 304 in this case as the basket is secured to the wall. In fact, the object of the prior art device 300 is to provide enough outward radial pressure to the vessel wall 310 to firmly secure it to the vessel wall so that it may be used as a tensioning device to advance other devices coaxially over it, to occlude the vessel and to anchor it firmly to the vessel wall. In these instances and for these applications, it may be advantageous to create an expansile element that exerts excessive outward radial force to the vessel wall to achieve the desired results in that particular application.

The vessel wall 310 may easily be damaged by the intended overexpansion or the inadvertent overexpansion of the braid, or other expansile element, in a vessel. This damage is illustrated in FIG. 13 by the area of hemorrhage or dissection 311 in the media of the blood vessel wall 310. This damage may incite the exuberant reparative effort of the blood vessel BV that results in restenosis. This damage caused by the uncontrolled expansion and distension of the blood vessel BV can stimulate a cascade of events in which smooth muscle cells and other pluripotential cells migrate toward the lumen and create a scar of sort that may occlude or severely narrow the vessel demanding further intervention at a later date. Addressing this dilemma is an object of the present disclosure.

Figure 14:
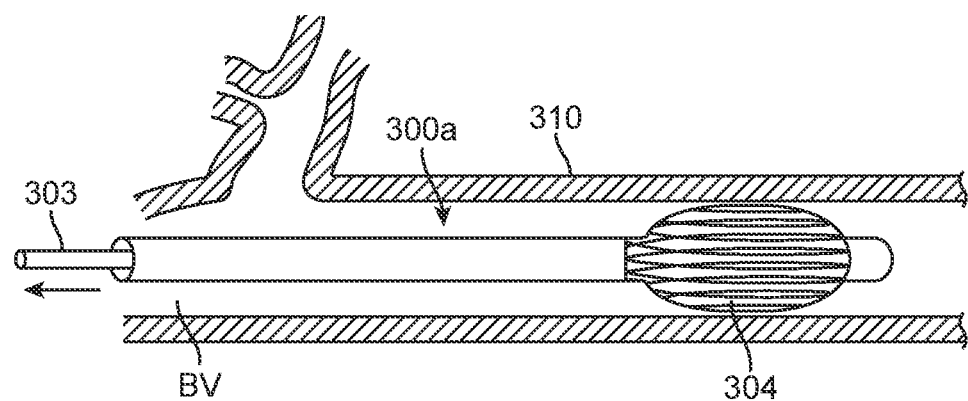
FIG. 14 shows a side view of a traction device expanded in a blood vessel, according to some embodiments.

The current inventor has conducted experiments have shown that damage to the arterial wall can be avoided by such a device if constructed of Nitinol wires treated to provide a combination of stiffness and flexibility that not only creates a limited amount of outward radial force against the wall, but also causes the braid to elongate when placed in smaller vessels. This limited radial force and elongation are illustrated by the present traction device 100*a* in FIG. 14. When the inner member 303 is retracted relative to the outer sleeve 302, the braid or other expansile element 304 expands to the vessel wall 310 but does not expand the wall 310. Instead, because of the combination of structural features, the braid or other expansile element 304 elongates and does not distend or damage the vessel wall as in FIG. 13. There is no hemorrhage or dissection 311 with the elongation in FIG. 14 as there is with the forceful radial expansion illustrated in FIG. 13. This lack of hemorrhage or dissection 311 may prevent the restenosis reaction from occurring. Generally, the traction device 300*a* may not anchor or serve as a tensioning means as in the prior art device 300, but the device of FIG. 14 may still function as a filter, clot traction device, or occluder.

It is important that the improved current device provide a consistent and balanced outward radial force over a fairly wide range of vessel diameters as well. In other words, the current device, because of a combination of structural elements, should provide a limited amount of outward radial force insufficient to damage the vessel wall which is independent of the vessel wall diameter over a range of vessel diameters.

While the current disclosure discusses the specific location of the elastomer and the elastomer free portion of the braid, there may in certain instances be a need for the elastomer to cover or be applied to only a minimal section of the braid. This may especially be true when complete occlusion is not desirable. In these instances, the devices may be constructed similarly to the above examples, with the elastomer free section comprising a majority or even all of the braid. The elastomer containing section may be small or absent in at least these cases. The elastomer containing section may be placed on the braid so that a portion of the funnel is impermeable, but the funnel apparatus would typically not obstruct or occlude flow.

Figure 15:
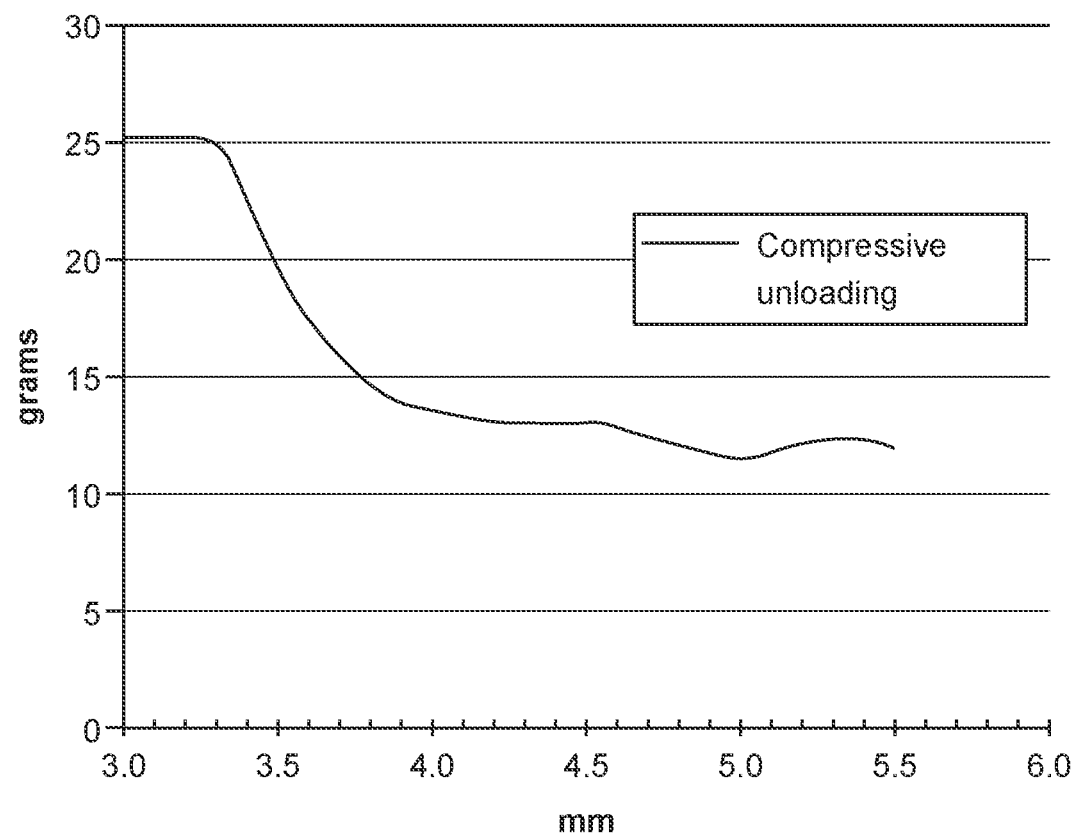
FIG. 15 shows a graph of compressive unloading for a traction device according to many embodiments.

The traction device 300a of the present disclosure may utilize 0.004" diameter Nitinol wires that have been heat treated to provide a combination of stiffness and flexibility and by varying the pics per inch, the number of wires, the shape of the wires, the crossing angle of the wires as well as the density of any elastomeric coating, if any, so that the expanded device will achieve a "programmed" outward radial force even if attempts are made to expand the device beyond the diameter of the vessel. As the graph in FIG. 15 demonstrates, a braid section fully expanded to 5.5 mm in a 5.5 mm vessel can create about 12 grams of outward radial force or compressive unloading. It can essentially create the same amount of outward radial force when expanded with the same degree of translation of the inner shaft relative to the outer shaft over a range of different sized vessels because the braid section elongates rather than expands outward as a result of the properties inherent in the Nitinol wires and the braid pattern. The linear relationship of the length of translation of the inner wire to the outer sleeve with the degree and outward force of expansion present in prior art devices can be overcome in the present traction device by the use a combination of the flexibility of the Nitinol wires which is a result of size of wires and material choice, by heat treating, the pics per inch, the number of wires in the braid, the crossing angle of the braid, the relative stiffness of the silicone or other elastomer amongst other items. Particularly, heat treating the Nitinol wires in a jammed state where the braid is compressed into the smallest diameter and elongated will generally cause the braid to display a minimal amount of outward radial force independent of the vessel size. Smaller and more flexible wires will also tend to cause the device to elongate rather than expand outward. Utilizing a small braid angle can be another important structural component to facilitate elongation vs. outward expansion and may be as important as other structural features. With a larger braid angle, where one wire crosses another, that approaches 90 degrees, the braid can resist collapsing and can maintain a relatively large amount of outward radial force. It can also resist elongation, which may be part of the collapsing process. With smaller braid angles, the tubular braid may not possess as much radial strength or outward radial force as the braid wires can tend to move relative to each other to even smaller angles resulting in elongation of the tubular braid. This elongation can be very important as it may prevent excessive outward radial force from being transmitted to the vessel wall and potentially damaging the wall. This improvement over the prior art traction devices (e.g., traction device 300) utilizing a combination of the structural features above can prevent damage to the vessel wall by providing an effective way to pull clot or other substance into a catheter, whether a standard catheter or a braided funnel catheter described herein. It may also be utilized in other non-balloon expansile devices as mentioned above.

For example, if the prior art traction device 300 were placed in a 5.5 mm diameter vessel and expanded to 5.5 mm so that it abuts the wall, it would provide a certain amount of outward radial force against the wall. If the same device were utilized in a 3.5 mm vessel and expanded to 5.5 mm diameter, the prior art traction device 300 may over-distend the wall of the vessel 2 mm or so to the 5.5 mm diameter creating a situation that may very easily cause damage to the vessel wall as previously illustrated in FIG. 12 which may result in restenosis and other negative events. Overexpansion such as in this example may be common as the prior art traction devices can be so delicate that they cannot be easily visualized by fluoroscopy during a procedure, so the operator expands the braid by "feel" which is inexact at best. Instead of under expanding the prior art traction device and being ineffective, the tendency may be to over expand it. An alternative to prevent this overexpansion and subsequent damage to the vessel wall is to size the expansile device to the size of the vessel and utilize a specifically sized device for each vessel treated. For a 5.5 mm vessel, one may use a device sized to provide a relatively low amount of outward radial force, and for a 3.5 mm diameter vessel, one may use another device sized to provide a relatively low amount of outward radial force to the vessel wall of that particular size in that case. This custom sizing can be effective in limiting the damage to the vessel wall, but can create stocking and inventory problems and may drive the cost of utilizing these devices upward as a facility must stock multiple different sized devices to cover the range of vessel sizes from 2 mm or so in the cerebral, coronary, and below the knee arterial circulation to 8-10 mm in the iliac artery to 16 mm in the iliac veins and even larger in the inferior vena cava and all sizes in between. Moreover, it may frequently be necessary to utilize the same type of device at different locations within the same patient, which may create the need for a catheter or device exchange which is time consuming and involves utilizing a new device for the second location which may cost thousands of dollars. In essence, the use of specifically sized devices that avoid damage to the vessel wall may demand the costly and time consuming use of two or more specifically sized devices in different vessels in the same patient rather than the serial use of one device which may safely and more time efficiently treat a wide range of sizes. Hence, there is a real need to control the outward radial pressure exerted on the vessel wall in expansile devices to prevent vessel wall damage such as this traction device, and also in embolic protection filters, occlusion devices, other traction devices as well as most any expansile device by "programming" the expansile force into the device to create as little outward radial force as possible over a wide range of diameters.

An elastomer may be provided to cover all or part of the braid 304, especially if the present traction device 300a is used as a vascular occluder, and may increase or decrease the outward radial force depending on the properties, thickness and consistency of the elastomer. A braid 304 of different programmed properties may be utilized in that instance.

Yet another way of controlling the outward radial force may be to utilize an elastic or elastomeric material, such as, but not limited to, silicone, urethane, neoprene, isoprene, Pebex, chloroprene and the like for the inner member or outer sleeve, so that the inner member stretches or the outer member compresses if attempts are made to over expand the device within a vessel. Instead of the excessive outward radial force being transmitted to the wall, in this case, it can be transmitted to the at least somewhat elastic inner member by stretching said member after a selected outward radial pressure is achieved by the braid or expansile component or by compressing the outer sleeve after a selected outward radial pressure is achieved by the braid or expansile component, or by utilizing both. As well, ways to elongate the braid may also be utilized with either ways to stretch the inner member and with ways to compress the outer sleeve, or both, to prevent outward radial force from being transmitted to the vessel wall beyond a selected level.

Furthermore, since the outward radial force is usually created in a linear relationship by pulling the inner member in relation to the outer sleeve, a spring in the handle of the device attached to the inner member may prevent the full expansion of the braid and limit the outward radial pressure. Hence, a spring may be used alone or in combination with any or all of the features listed above to limit the outward radial pressure.

Figure 16:
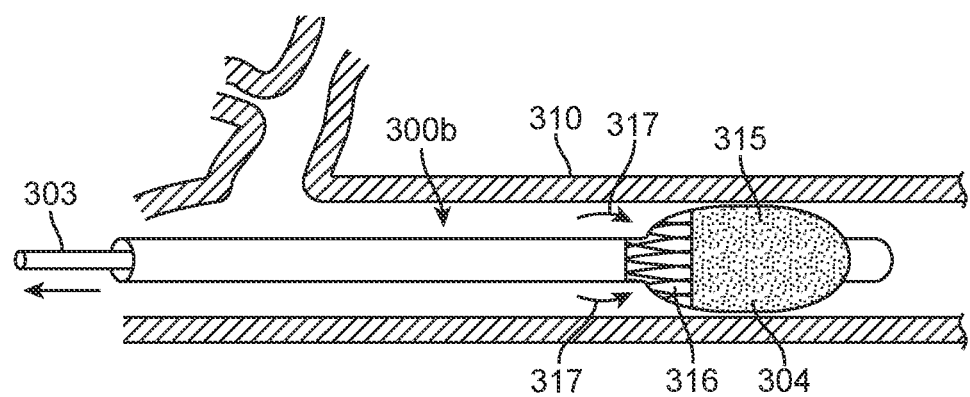
FIG. 16 shows a side view of another traction device expanded in a blood vessel, according to some embodiments.

Yet another way of providing minimal outward radial force to the vessel wall 310 with an expandable braid device 304, as illustrated in FIG. 16, is to provide an impermeable or partially impermeable elastomer or membrane 315 on at least the distal section of the braid 304 and an elastomer or membrane free section 316 proximally so that the patient's blood pressure may be transmitted beneath the impermeable or partially impermeable aspect of the braid 315 as shown by arrows 317. The transmitted blood pressure may enhance the expansion of the expandable basket 304 against the vessel wall 310. Hence, as in the apparatus 300b illustrated in FIG. 16, most of the outward radial force of the expandable basket 304 to the wall of the blood vessel 310 may be from the patient's own blood pressure and not from the inherent outward radial force of the expandable braid 304. In essence, the membrane or elastomer 315 may preferably be combined with either one or more of the previously discussed structural features of the braid to accomplish this version. This combination of structural features including the features that cause the braid to lengthen rather than expand and the membrane 315 may minimize the chance of damage to the blood vessel 310 by excessive outward radial force as is present in prior art devices.

Referring back to FIGS. 3 and 4, a dilator or obturator 220 may be used in conjunction with the funnel catheter or occlusion device 100a. Since in the contracted configuration, the braid 200 is on the outside of the inner sleeve 196 and exposed to the vessel wall 210, there can be the potential for the braid 200 to engage the vessel wall 210 and damage the intima as the braid 200 may not be as smooth as a usual smooth catheter exterior. The leading edge of the braid 200 at the tip of the catheter may particularly have a lower smoothness. Hence, it may be advantageous to provide a way to create a smoother leading edge of the catheter. Usually, an obturator or inner catheter 220 can be utilized coaxially within the catheter and over the guide wire to provide a more or less smooth transition from the guide wire (0.014" to 0.035") to the catheter shaft (0.044" to 0.069"). In standard catheters, this configuration of guide wire, obturator or inner catheter 220, and then the catheter may be adequate but with the leading edge of the current catheter comprising a section of braid and two wall thicknesses because of the inner and outer sleeves, there still may be some exposed braid over the obturator or inner catheter which may engage the vessel wall. To create a smooth transition and protect the wall from damage or an abrasion of the intima by the exposed braid, the obturator or dilator 220 may be adapted as shown in FIG. 4 to fill the 0.006"-0.010" difference between the OD of the contracted funnel catheter and then OD of the obturator or inner catheter.

Figure 5:
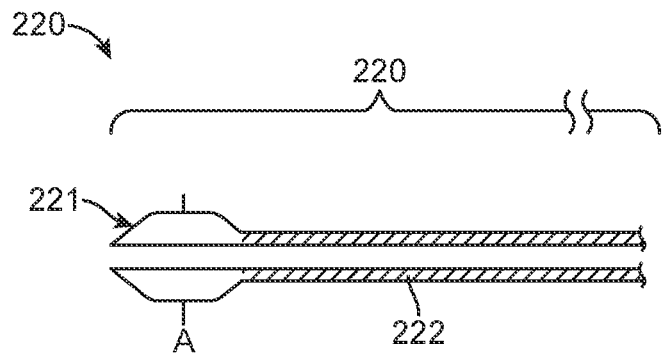
FIG. 5 illustrates a side view of a dilator usable with an occlusion device, in accordance with some embodiments.

FIG. 5 shows that the dilator or obturator 220 may be sized so that it fits within the inner diameter of the funnel catheters 100 and 100a previously described, but with an oversized tip or distal end that extends beyond the distal end of the funnel catheter when the funnel catheter is in a contracted or tubular configuration. Since the distal tip 221 of the dilator 220 should be just as large as the outer diameter (OD) of the funnel catheter 100, 100a and oversized relative to the inner diameter (ID) of the funnel catheter 100, 100a, it should be compressible to insert it through the hub end of the funnel catheter 100, 100a and to remove it from the funnel catheter 100, 100a once the funnel catheter 100, 100a is in place at a target location in the vasculature. To accomplish this, the dilator 220 can have novel features that can provide for protection against injury to the arterial wall by the braided section and allow the oversized tip 221 to be inserted and withdrawn through the funnel catheter even though the ID of the funnel catheter is smaller than the OD of the tip of the dilator.

Figure 6:
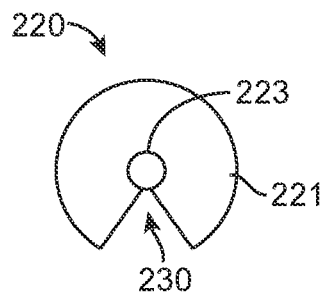
FIG. 6 illustrates a cross sectional view of the dilator of FIG. 5 at a position A in FIG. 5.
Figure 7:
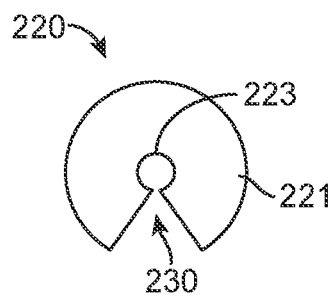
FIG. 7 illustrates a cross sectional view of the dilator of FIG. 5 at the position A in FIG. 5, the dilator having an additional cutout.
Figure 8:
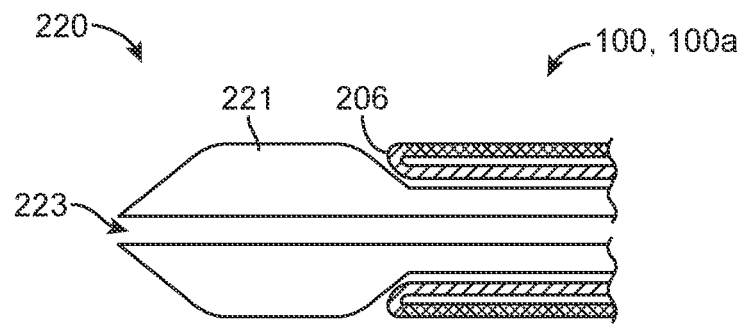
FIG. 8 illustrates a side view of the dilator of FIG. 5 inserted into the funnel catheter of FIGS. 3 and 4 in the contracted configuration.
Figure 9:
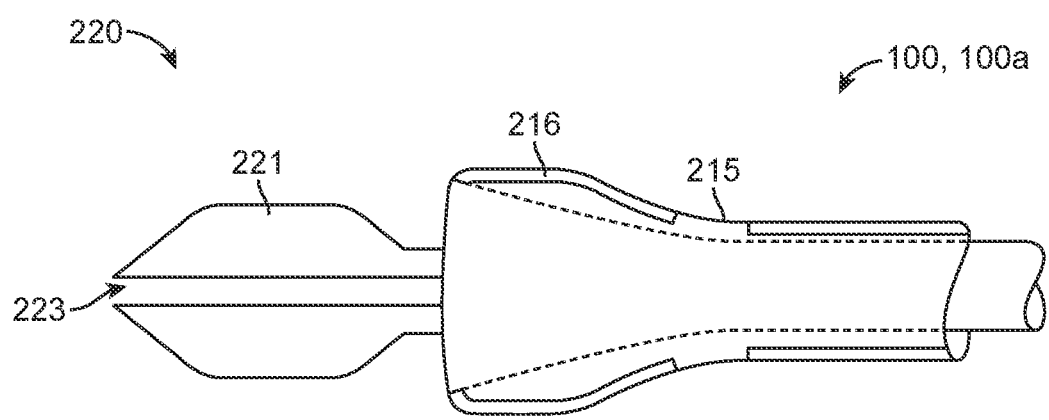
FIG. 9 illustrates a side view of the dilator of FIG. 5 inserted into the funnel catheter of FIGS. 3 and 4 in the expanded configuration.

The shaft 222 of the dilator 220 may be sized to fit within the ID of the funnel catheter inner sleeve 196. The tip 221 of the dilator 220 may be the same size as the OD of the funnel catheter 100, 100a. The dilator 220 comprises a lumen 223 for receiving a guide wire. So that the tip of the dilator 220 may fit through the ID of the funnel catheter 100, 100a, it must be compressible. One way of providing compressibility may be to utilize a softer durometer substance within the tip. Another way may be to place a notch or a wedge shaped cutout 230 in the tip as demonstrated in FIG. 6 which is a cross section of FIG. 5 at a location A. Still another way may be to enlarge the guide wire lumen 223 to accommodate the compression needed for the larger tip to fit into the smaller lumen or to connect the guide wire lumen 223 to the notch 230 as demonstrated in FIG. 7. Utilizing one or more of these ways can allow the larger tip 221 to compress so that it may be inserted and removed through the smaller catheter lumen. Placing the obturator device 220 through the hub or proximal end of the catheter 100, 100a should not be problematic as means to compress the tip 221 outside the body are readily available and may comprise just ones finger and thumb or a special tool to receive the dilator tip and compress it to a smaller size by advancing it into a rigid funnel like structure. When placed through the catheter lumen as demonstrated in FIG. 8, the oversized tip 221 of the dilator 220 may cover the leading edge of the funnel catheter tip 206 and prevent any injury to the vessel wall that may be cause by the exposed braid otherwise. By angling the lumen 223 toward the notch 230 at the end of the dilator 220, the guide wire can be subtlety directed over that notch 230 and toward the wall of the vessel that one does not want the gap to encounter, hence "protecting" the gap or partially covering it and directing that portion of the tip away from the vessel wall. Removing the oversized tip can be facilitated by deploying the funnel apparatus of the funnel catheter as illustrated in FIG. 9 initially and then retracting the oversized, but compressible, dilator tip into the catheter shaft. While the primary objective of the oversized tip of the dilator 220 may be to protect the vessel wall from the catheter tip, the oversized tip 221 may also be utilized to retract thrombus or other material into the catheter. If utilized in a standard catheter, for example, the oversized but compressible dilator tip 221 and dilator 220 may be removed by simply retracting it into and out of the catheter shaft.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a bodily vessel, the method comprising:
   introducing a catheter toward a target site in the bodily vessel;

advancing a traction apparatus having an inner shaft, a tubular outer sleeve and an expandable mesh braid, from within an inner lumen of the catheter;

expanding the expandable mesh braid within the target site, wherein expanding comprises increasing an outer diameter of the expandable mesh braid less than a distance of a translation of the inner shaft and the tubular outer sleeve relative to one another;

elongating the expandable mesh braid axially and applying less than about 25 grams of outward radial force on the bodily vessel to minimize radial expansion of the bodily vessel, thereby minimizing distending or damaging the bodily vessel when the expandable mesh braid is expanded in the bodily vessel; and retracting the expanded mesh braid axially to capture and retract material in the target site into the inner lumen of the catheter.

2. The method of claim 1, wherein the bodily vessel comprises a blood vessel.

3. The method of claim 2, wherein the captured and retracted material comprises a blood clot or a thrombus.

4. The method of claim 1, wherein expanding the expandable mesh braid comprises expanding the expandable mesh braid to appose an outer surface of the expandable mesh braid against an inner wall of the bodily vessel.

5. The method of claim 4, wherein the expandable mesh braid comprises a plurality of wires configured to exert the predetermined amount of radially outward force when the expandable mesh braid is expanded in the bodily vessel.

6. The method of claim 5, wherein the plurality of wires is configured to exert the predetermined amount of radially outward force independently of an inner diameter of the bodily vessel.

7. The method of claim 1, wherein expanding the expandable mesh braid comprises expanding the expandable mesh braid to a predetermined outer diameter.

8. The method of claim 1, wherein the expandable mesh braid has a shape memory characteristic.

9. The method of claim 1, wherein expanding the expandable mesh braid comprises translating the inner shaft and the tubular outer sleeve of the traction apparatus relative to one another.

10. The method of claim 9, wherein a degree of a translation of the inner shaft and the tubular outer sleeve relative to one another has a non-linear relationship with an outer diameter of the expandable mesh braid.

11. The method of claim 9, wherein a degree of a translation of the inner shaft and the tubular outer sleeve relative to one another has a non-linear relationship with a radially outward pressure exerted by the expandable mesh braid.

12. The method of claim 1, wherein the expandable mesh braid has an impermeable or partially impermeable elastomer or membrane on at least a distal section of the expandable mesh braid.

13. The method of claim 12, wherein expanding the expandable mesh braid comprises transmitting blood pressure beneath the impermeable or partially impermeable elastomer or membrane to expand and elongate the expandable mesh braid.

14. The method of claim 1, wherein expanding the expandable mesh braid comprises applying pressure between about 0.5% to about 10% of a radially outward force of blood pressure on the bodily vessel.

15. A traction apparatus for treating a bodily vessel, the traction apparatus comprising:

an inner shaft having a distal end;

a tubular outer sleeve coaxially disposed over the inner shaft and having a distal end; and an expandable mesh braid coaxially disposed over the inner shaft and coupled to the distal end of the inner shaft and the distal end of the tubular outer sleeve, wherein the expandable mesh braid, in the expanded configuration, has a proximal tapered portion and a distal tapered portion, wherein the expandable mesh braid is configured to elongate axially and apply a radially outward force of less than 25 grams independent of the vessel wall diameter on the bodily vessel to minimize radial expansion of the bodily vessel, thereby minimizing distending or damaging the bodily vessel when the expandable mesh braid is expanded in the bodily vessel, and wherein the expandable mesh braid is configured to capture and retract material in the target site or occlude the bodily vessel;

wherein the inner shaft and the tubular outer sleeve are translatable relative to one another to shift the expandable mesh braid between contracted and expanded configurations by withdrawing the inner shaft relative to the tubular outer shaft, wherein an outer diameter of the expandable mesh braid is configured to increase less than a distance of a translation of the inner shaft and the tubular outer sleeve relative to one another when the expandable mesh braid is expanded to its expanded configuration.

16. The traction apparatus of claim 15, wherein the expandable mesh braid comprises a plurality of wires.

17. The traction apparatus of claim 16, wherein the plurality of wires is configured to provide a combination of stiffness and flexibility.

18. The traction apparatus of claim 16, wherein the plurality of wires comprises a plurality of Nitinol wires.

19. The traction apparatus of claim 16, wherein the plurality of wires is configured to exert the predetermined amount of radially outward force independently of the inner diameter of the bodily vessel.

20. The traction apparatus of claim 15, wherein the expandable mesh braid in the expanded configuration is configured to expand to appose an inner wall of the bodily vessel while minimizing resultant expansion of the bodily vessel.

21. The traction apparatus of claim 15, wherein the expandable mesh braid is expandable to a predetermined outer diameter to apply the predetermined amount of radially outward force.

22. The traction apparatus of claim 15, wherein the expandable mesh braid has a shape memory characteristic.

23. The traction apparatus of claim 15, wherein a degree of a translation of the inner shaft and the tubular outer sleeve relative to one another has a non-linear relationship with an outer diameter of the expandable mesh braid.

24. The traction apparatus of claim 15, wherein a degree of a translation of the inner shaft and the tubular outer sleeve relative to one another has a non-linear relationship with a radially outward pressure exerted by the expandable mesh braid.

25. The traction apparatus of claim 15, wherein the expandable mesh braid has an impermeable or partially permeable elastomer or membrane on at least a distal section of the expandable mesh braid and a permeable portion.

26. The traction apparatus of claim 25, wherein the permeable portion is configured to transmit blood pressure beneath the impermeable or partially impermeable elastomer or membrane to expand and elongate the expandable mesh braid.

27. The traction apparatus of claim 15, wherein the bodily vessel comprises a blood vessel.

28. The traction apparatus of claim 15, wherein the inner shaft comprises a spring.

29. The traction apparatus of claim 15, wherein the expandable mesh braid comprises flexible nitinol wires heat treated when the expandable mesh braid is in a collapsed state.

30. The traction apparatus of claim 15, wherein the expandable mesh braid comprises braid crossing angles less than about 90 degrees.

\* \* \* \* \*